(12) United States Patent
Robertson, Jr. et al.

(10) Patent No.: US 8,223,338 B2
(45) Date of Patent: Jul. 17, 2012

(54) OPTICAL PATH LENGTH SENSOR AND METHOD FOR OPTIMAL ABSORBANCE MEASUREMENTS

(75) Inventors: Charles W. Robertson, Jr., Centreville, DE (US); Damian W. Ashmead, Middletown, DE (US); Thomas A. Tokash, Chesapeake City, MD (US)

(73) Assignee: Nanodrop Technologies, LLC, Wilmington, DE (US)

( * ) Notice: Subject to any disclaimer, the term of this patent is extended or adjusted under 35 U.S.C. 154(b) by 470 days.

(21) Appl. No.: 12/572,892

(22) Filed: Oct. 2, 2009

(65) Prior Publication Data

US 2010/0085571 A1    Apr. 8, 2010

Related U.S. Application Data

(60) Provisional application No. 61/102,740, filed on Oct. 3, 2008, provisional application No. 61/102,553, filed on Oct. 3, 2008, provisional application No. 61/102,560, filed on Oct. 3, 2008.

(51) Int. Cl.
*G01N 21/00* (2006.01)
*G01N 1/10* (2006.01)

(52) U.S. Cl. ........................... 356/440; 356/246

(58) Field of Classification Search ..................... None
See application file for complete search history.

(56) References Cited

U.S. PATENT DOCUMENTS

| | | |
|---|---|---|
| 5,009,488 A | 4/1991 | Fay et al. |
| 5,739,432 A | 4/1998 | Sinha |
| 6,628,382 B2 | 9/2003 | Robertson |
| 6,809,826 B2 | 10/2004 | Robertson |
| 7,365,852 B2 | 4/2008 | Schleifer |
| 7,397,036 B2 | 7/2008 | Robertson et al. |

*Primary Examiner* — Gregory J Toatley
*Assistant Examiner* — Amanda Merlino
(74) *Attorney, Agent, or Firm* — Michael C. Staggs

(57) ABSTRACT

An apparatus is described in which an optical fiber is mounted within a fiber optic holder which includes the non-rotating shaft of a linear actuator. The fiber holder may be held captive in order to restrain the fiber holder and, consequently, the fiber mounted therein, from rotating during operation of the linear actuator, thereby resulting in linear travel with minimal rotational effects and minimal change in optical alignment of the fiber during travel. In addition, an optical path length sensor in conjunction with an optimized absorbance method of operation is utilized herein to provide micron precision of the displacement between respective receiving and transmission fibers so as to enable precise absorbance measurements from about 0.005 up to about 2.0 Absorbance Units for any given path length.

16 Claims, 17 Drawing Sheets

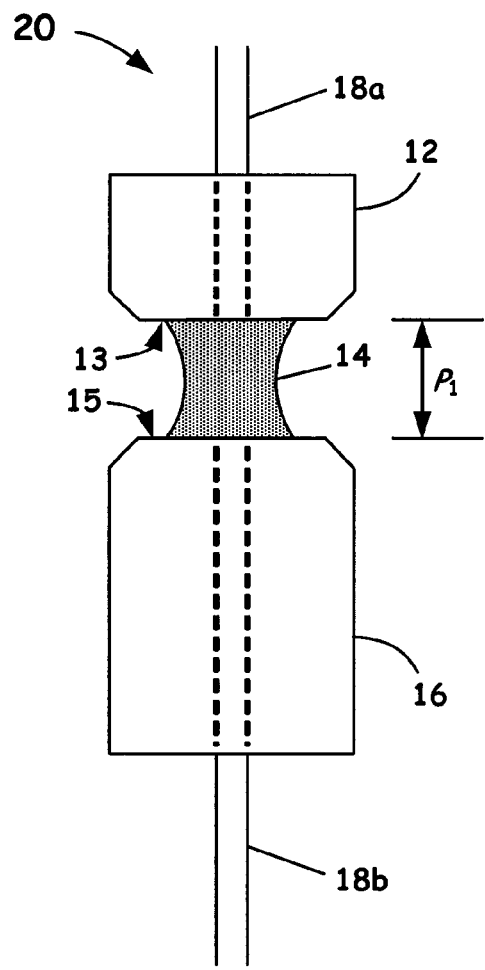
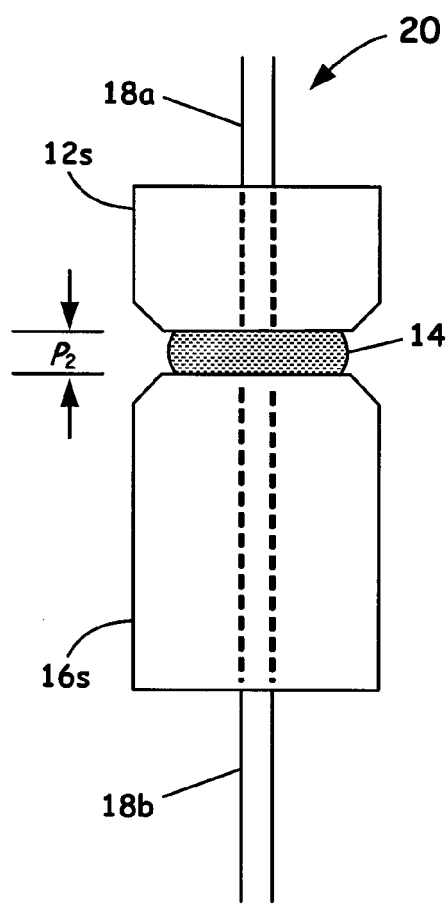
FIG. 2A
FIG. 2B

OPTICAL PATH LENGTH SENSOR AND METHOD FOR OPTIMAL ABSORBANCE MEASUREMENTS

RELATED APPLICATION

This application claims the benefit of U.S. Provisional Application No. 61/102,740, entitled: "Optical Path Length Sensor for Measuring Absorbance," and U.S. Provisional Application No. 61/102,553, entitled: "Method and Apparatus for a Linear Actuator and Fiber Optic Light Delivery and Collection System," and U.S. Provisional Application No. 61/102,560, entitled: "Method for Optimum Optical Absorbance Measurements," all of which were filed Oct. 3, 2008, and all of which are incorporated herein by this reference.

FIELD OF THE INVENTION

This invention relates to the field of spectrophotometers and related instruments for characterizing small-volume samples. More particularly, the invention relates to fiber optic light delivery and collection systems and a means for optimizing measurements within such instruments.

BACKGROUND OF THE INVENTION

Liquids, mixtures, solutions and reacting mixtures are often characterized using optical techniques such as photometry, spectrophotometry, fluorometry, or spectrofluorometry. In order to characterize samples of these liquids, conventional methods and apparatus generally employ a sample-holding vessel or cell, for instance, a cuvette, which has two or more sides of optical quality so as to permit the passage of those wavelengths needed to characterize a liquid contained therein.

Unfortunately, biological sampling techniques often yield very small quantities of material for analysis. Accordingly, absorbance and fluorescence measurements with minimal consumption of sample material have become paramount. When dealing with very small sample volumes—for instance, from 1 to 2 microliters—it is difficult to create cells or cuvettes small enough to be filled and permit the industry standard 1 cm optical path to be used. It is also difficult and/or time consuming to clean these cells or cuvettes for use with another sample. Thus, conventional methods of photometry, spectrophotometry, fluorometry, spectrofluorometry, etc. are impractical when dealing with small sample volumes, such as of biological samples produced by laser-capture microdissection.

In the case of photometry or spectrophotometry, the usual quantity of interest is absorbance, A, which, for liquid samples, is most often defined as:

$$A = -\log_{10}(T) = -\log_{10}(I_R/I_0)$$  Eq. 1;

where T is the transmittance, $I_R$ the intensity (e.g., power) of light transmitted through the sample being measured and $I_0$ is the intensity of light transmitted through a blank or reference sample. Most commonly, the absorbance value is measured in a cell or cuvette with a 1 cm path length. However, Lambert's Law states that for a collimated (all rays approximately parallel) beam of light passing through a homogeneous solution of uniform concentration the absorbance, A, is proportional to the path length through the solution. For two light path lengths $P_1$ and $P_2$, $$\frac{A_1}{A_2} = \frac{P_1}{P_2};$$  Eq. 2 where $A_1$ and $A_2$ are the absorbance values determined at path lengths $P_1$ and $P_2$, respectively. Further, absorbance is a function of absorptivity, c, path length, P, and analyte concentration, c, through the relation:

$$A = \epsilon c P$$  Eq. 3.

Thus, it is often possible to measure absorbance using path lengths other than 1 cm and to use the results to calculate concentration or absorptivity or, if desired, to correct absorbance to the equivalent value for a 1 cm path for more-ready comparison with conventional data.

U.S. Pat. Nos. 6,809,826 and 6,628,382, each of which is incorporated herein by reference in its entirety, teach methods and apparatus of spectrophotometry or the like on extremely small liquid samples. The sample path lengths in the range of 0.2 to 2 mm taught in the above-referenced patents can be used to generate absorbance values that can be easily corrected to the 1 cm path equivalent.

According to the teachings in the above referenced patents, a sample droplet is held between two opposing substantially parallel surfaces by interfacial tension and one surface is controllably moved toward and away from the other. To provide and transmit light through the droplet for measurement, and to collect light for measurement, at least one of the surfaces may have a portion of optical measurement quality. This may be accomplished by providing at least a portion of at least one of the surfaces as a polished end of an optical fiber, wherein each such optical fiber may be finished flush with the surrounding surface portion. Typically, such surrounding surface portion often includes the surface of an end of a standard fiber optic connector or other fiber holder.

As disclosed in the above-noted patents, to make a measurement of less than about 2 micro-liters of a sample, such an amount is pipetted directly onto one of the surfaces, for instance the lower surface 15 shown in FIGS. 1A and 2A. An upper surface, surface 13, subsequently moves down so as to engage the sample and then moves upward and away from the lower surface, thus using interfacial tension to adhere to lower surface 15 and upper surface 13, wherein surface tension forms a liquid column 14 of mechanically controlled path length (see FIGS. 1A-1B and FIGS. 2A-2B). The shape and nature of the upper and lower surfaces, i.e., surface 13 and surface 15, serve to maintain the sample within a pre-defined optical path. One of the surfaces, e.g., surface 13, can be swung clear of the other for easy cleaning between measurements on different samples.

Moreover, a differential absorbance path can be employed, as shown in FIGS. 1A and 1B as well as in FIGS. 2A-2B. By measuring transmitted light intensity I at each of one or more path lengths, the difference in transmitted intensity can be used in conjunction with the known path length difference to calculate the sample absorbance. Measurements are taken as shown in FIG. 1A, where sample 14 is shown with a relatively long light path length $P_1$ through the sample and as in FIG. 1B where sample 14 is shown with a relatively short light path length $P_2$ through the sample. These path lengths are measured between two surfaces mutually facing one another, as discussed above, e.g., between surface 13 of an upper member 12 and surface 15 of a lower member 16. During measurements, light is delivered into the sample through one of the two surfaces and the proportion of the light transmitted through the sample is collected from the sample through the other one of the surfaces. The upper and lower members may be referred to as upper and lower anvils or pedestals, respectively. However, while anvils or pedestals are beneficial configurations, it is to be noted that such terminology does not express or imply any particular geometric form for the upper and lower members.

The difference in light path length $\Delta P$ ($=P2-P1$) may be used to calculate the optical absorbance of the sample 14 shown in FIGS. 1A-1B and FIGS. 2A-2B, since $\Delta P$ may frequently be known with a greater degree of accuracy and precision than either of $P_1$ and $P_2$. The path length itself may be controlled by a movement means, such as, for example, by a solenoid mounted below the apparatus, the plunger of which can bear on a pin of a hinged swing arm holding the upper member. The up and/or down movement of the plunger causes the swing arm to rotate slightly about its hinge, thus causing the upper member, displaced from the pin, to move up and/or down so as to vary the light path length through the sample.

FIGS. 2A and 2B specifically shows an additional arrangement of the previously described apparatus in which the upper and lower members include optical fiber connectors or holders and in which a first optical fiber 18a passes through the first member and a second optical fiber 18b passes through the second member. Light is delivered into the sample from one of the two optical fibers and the proportion of the light transmitted through the sample is collected from the sample by the other one of the optical fibers.

Accordingly, the configurations shown in the figures described above enable differences in transmitted intensity to be used in conjunction with known differences in path length through a desired sample in order to calculate the sample's absorbance at one or more wavelengths of interest.

When sample absorbance, A, is high, transmission, T, through the sample is low, and vice versa. One frequently desires to have a sufficiently concentrated sample or a sufficiently long path length in order to provide an absorbance of sufficient magnitude to be measurable. If the absorbance is too low, then so-called "shot" noise from the relatively high level of transmitted light may interfere with the measurement. On the other hand, providing a sample with too great of an absorbance can cause the level of measured transmitted light to be too low, whereby electronic or other system background noise can preclude or obscure accurate determination of absorbance value. Such competing effects suggest that there will be an optimal level of absorbance at which the signal-to-noise of absorbance can be maximized.

Accordingly, there is a need to provide instruments that can rapidly vary the absorbance of a sample by varying the light path length so as to assure absorbance measurements with optimal signal-to-noise characteristics. Moreover, to also assure optimal signal-to-noise characteristics, there is an additional need for precisely controlling the position of the respective optical elements, such as, for example, a pair of optical fibers so as to not only minimize circular error resulting from the instrument but also for precise measurement of variable path lengths (e.g., $P_1$ and $P_2$) obtained for a sample while held in constrained surface-tension mode positions so as to accurately calculate $\Delta P$ and thus accurately provide for obtained absorbance and other related instrument measurements. The present invention is directed to such a need.

SUMMARY OF THE INVENTION

The present invention is directed to an optical apparatus for measuring an optical property of a sample that includes: a first pedestal surface coupled to a first optical conduit having a transmitting end; a base plate; a second pedestal surface mechanically coupled to the base plate and configured to receive a first liquid sample, the second pedestal surface being coupled to a second optical conduit having a receiving end, wherein the second pedestal further is operable so as to adjust a separation between the first and the second pedestal at a variable distance (P) to pull the first liquid sample into a column so as to be contained by surface tension, thereby providing an optical path with the transmitting end of the first optical conduit and the receiving end of the second optical conduit for photometric or spectrometric measurement; and a board configured with a sensor to provide feedback so as to enable precision displacement between the first and the second pedestal surfaces so as to enable the variable distance (P), the board further configured to enable holding a linear actuator motor body to the apparatus and thus:

a) permit translational movement of the circuit board together with the second optical conduit parallel to the axis of second optical conduit, and b) prevent rotation of the circuit board and the second optical conduit with respect to the apparatus as a whole; thereby resulting in linear travel with minimal rotational effects and minimal change in optical alignment of second optical conduit with respect to the first optical conduit.

Embodiments may further include: a cylindrical externally threaded portion of the optical fiber holder; a nut having an internally threaded portion engaged with the externally threaded portion of the optical fiber holder; and a motor mechanically coupled to the nut and operable so as to rotate the nut so as to cause the optical fiber holder to move so as to adjust the distance, P, wherein the linear actuator comprises the motor, the nut and the optical fiber holder. Some embodiments may further include: a mounting plate, and an adapter bushing mechanically coupled to the mounting plate by a slidable coupling and affixed to the optical fiber holder, wherein the adapter bushing prevents rotation of the optical fiber holder during rotation of the nut.

An additional aspect of the present invention includes a method of measuring a chemical concentration of a material that includes the steps of: determining a target optical absorbance value so as to provide an optimal signal-to-noise ratio for a measurement of optical absorption; experimentally determining an optimal light path length through the material corresponding to the target optical absorbance value; setting a light path length through the material substantially equal to the determined optimal light path length; measuring optical absorption through the set light path length of the material; and calculating the chemical concentration of the material from a known absorptivity of the material, the set light path length and the measured optical absorption through the set light path length of the material.

BRIEF DESCRIPTION OF THE SEVERAL VIEWS OF THE DRAWING

The above noted and various other aspects of the present invention will become apparent from the following description which is given by way of example only and with reference to the accompanying drawings, not drawn to scale, in which:

FIGS. 2A and 2B are two views of a second apparatus for measuring absorbance through a liquid sample maintained between two surfaces by interfacial tension; wherein each of the surfaces comprises, in part, an end of a respective optical fiber.

DETAILED DESCRIPTION

Figure 1A:
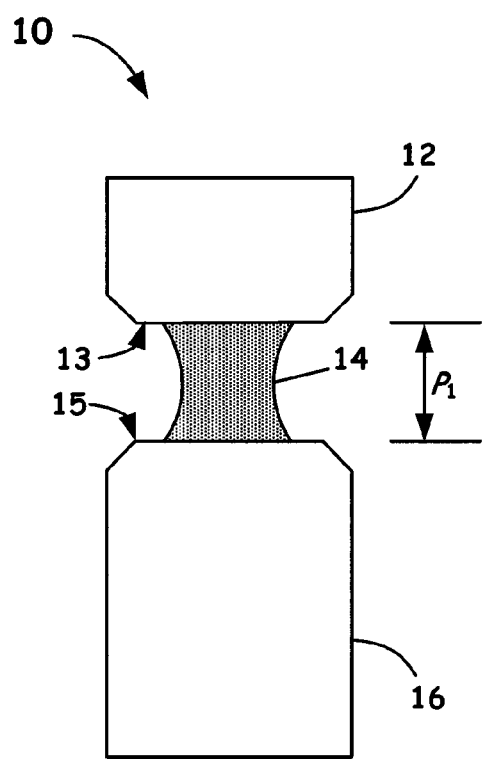
FIGS. 1A and 1B illustrate two views of an apparatus for measuring absorbance through a liquid sample maintained between two surfaces by way of interfacial tension.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Moreover, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The present invention is directed to an optical instrument and optimized method for measuring an analyte in a sample, which includes fluorometric, photometric, spectrophotometric and/or spectrofluorometric analysis of desired liquids contained in a free-space environment (e.g., a surface-tension-held environment).

In typical operation, directed optical radiation is transmitted through a solution or suspension held in column by surface tension and the incident light is diminished by the absorption of light by colored compounds and/or the scattering of light rays by particulate matter. Such an invention has many uses; it can be used to study pigmented molecules, to monitor the density of bacteria in a culture, and to follow the progress of an enzymatic reaction.

In making measurements, the present invention, in order to accomplish the creation of a variable path length and to eliminate the circular error of the apparatus swing arm, as described herein, at least one of the optical conduits (e.g., an optical fiber) can be axially mounted in a transducer (e.g., a linear transducer). A resultant path length from variable pathlengths can be determined from a combination of the motor motion and the output of a sensor, often an eddy current sensor that can be coupled to the end of the motor screw.

As one example embodiment, a circuit board having such an Eddy current sensor can not only serve as a transducer for measuring a path-length but also as a rotational inhibitor for the drive (i.e., a screw) that carries the lower optical conduit (e.g., a receiving optical fiber). Moreover, the circuit board of the present invention is coupled to the lower optical conduit and has slots that ride on special fasteners that hold the linear actuator motor body to the apparatus so as to provide a means to keep such a fastener from rotating. The circuit board also carries a coil that forms a drive element of an eddy current sensor using the back plate of the actuator motor as the object in which the Eddy currents are generated. The changing circuit impedance resulting from the spacing of the circuit board inductor relative to the back of the actuator motor changes the resonant frequency of the circuit and a digital circuit counts the pulses in a time interval to determine the board to motor spacing and thus accurate desired path lengths.

By use of the novel configurations briefly described above and as detailed herein, a method of operation of the present invention then further assures absorbance measurements having optimal signal-to-noise characteristics.

Accordingly, the novel integrated apparatus of the present invention provides for an instrument that can measure absorbances from about 0.005 up to about 2.0 Absorbance Units for any given path length via the amount of light passing through a surface-tension constrained sample configured as sample volumes of less than about 2 μ-liters (i.e. having path lengths of down to about 10 microns, more often down to about 50 microns).

Specific Description

Figure 3A:
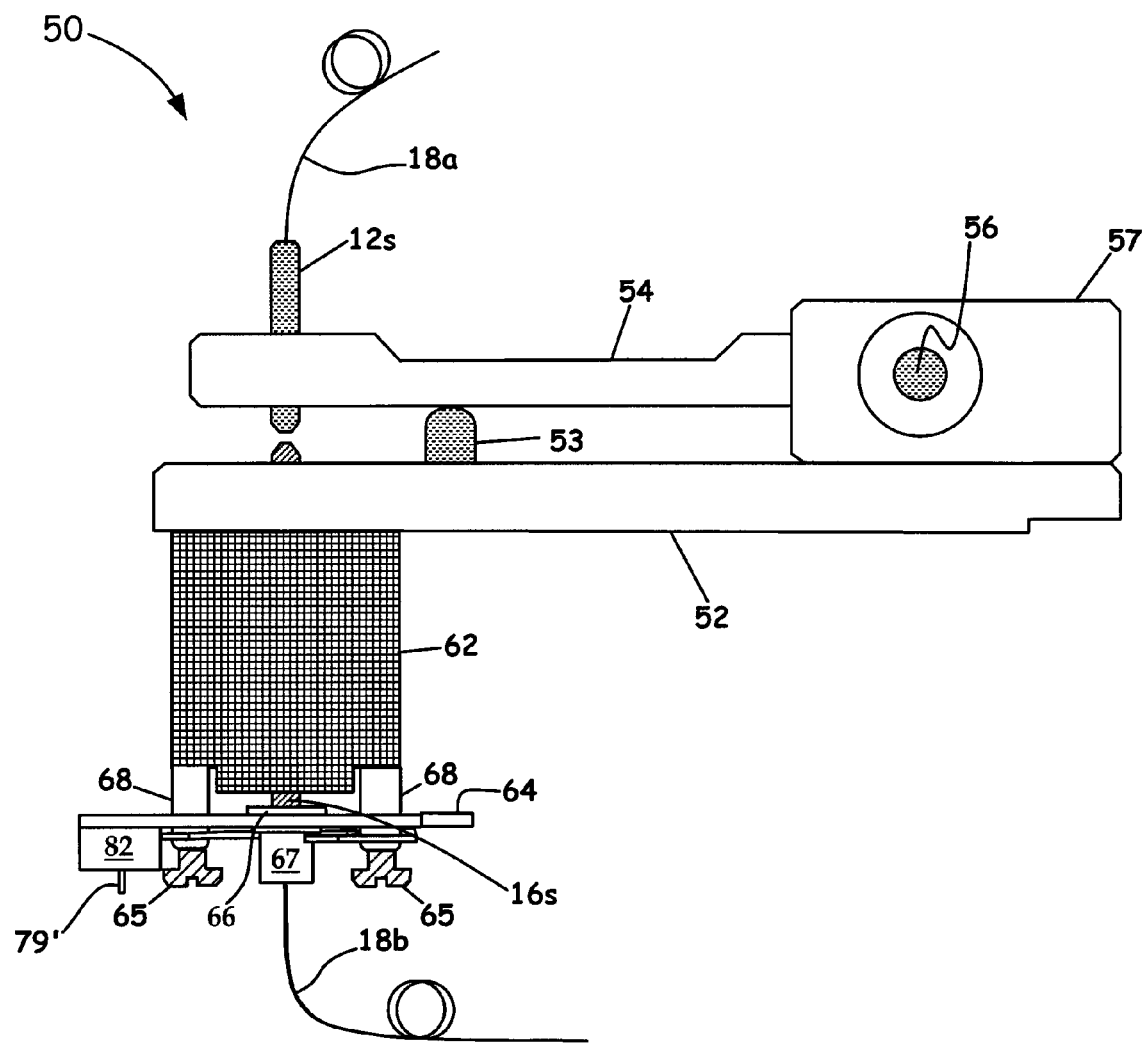
FIG. 3A shows a side view of an example embodiment of the present invention beneficially shown in a closed position.
Figure 3B:
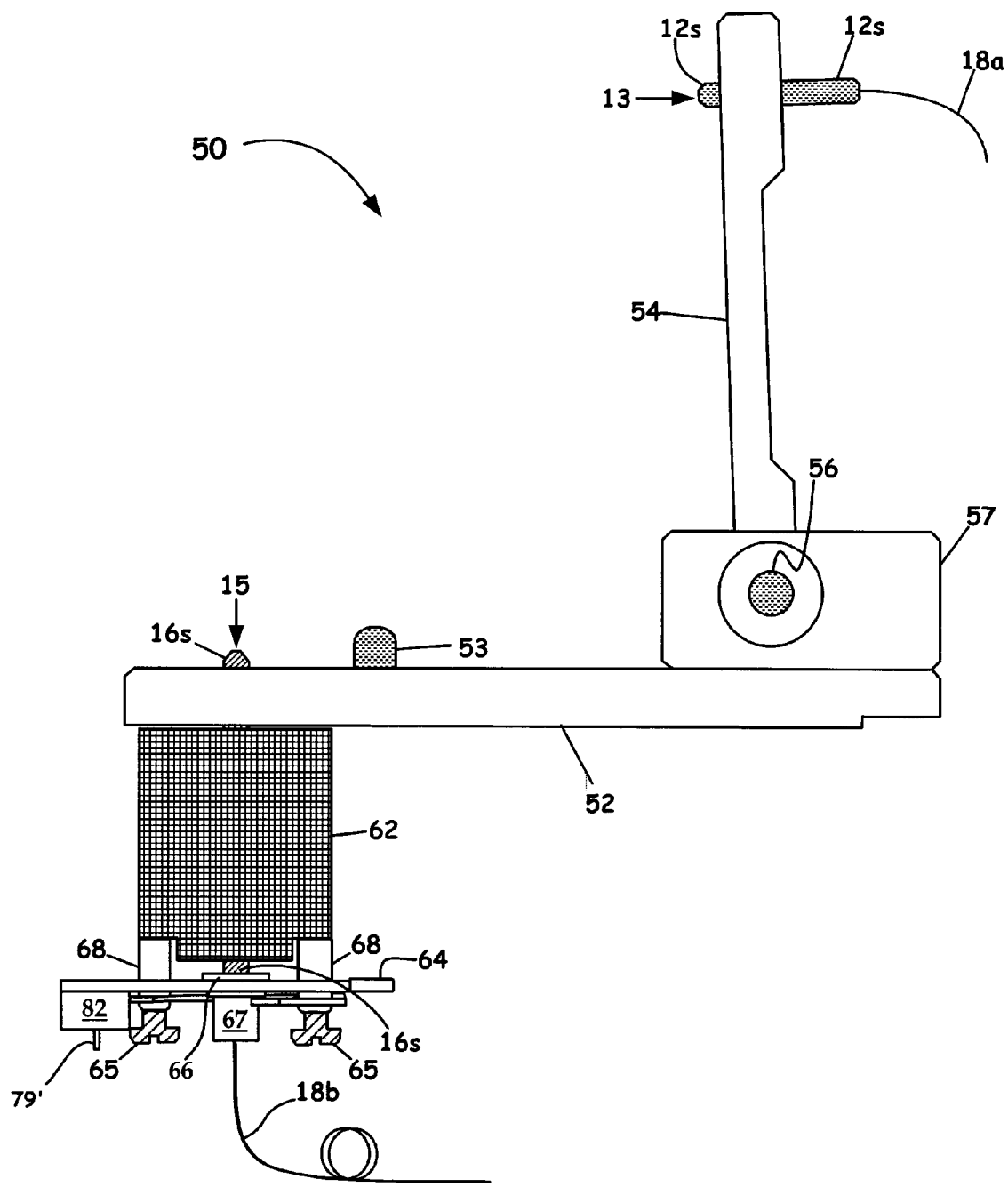
FIG. 3B shows a side view of an example embodiment of the present invention beneficially shown in an open position.

Turning now to the drawings, FIGS. 3A-3B are side views of an example apparatus in accordance with an embodiment of the invention. In particular, the apparatus, as illustrated in FIG. 3B and generally designated by the reference numeral 50, is shown in an "open" position in which a liquid drop analyte or reference sample, (of less than about 10 μl, more often less than about 2 μl, is dispensed or aspirated onto a lower platform surface 15. As discussed in more detail below, such an "open" position enables easy access to the ends of the surfaces, e.g., surface 15, which contain the liquid samples and also enables a user to easily clean such surfaces and to mount a new sample within the apparatus when desired.

Thus, in the "open position" of FIG. 3B, the dispensing of a liquid sample of less than about 10 μl, often less than about 2 μl, can often be delivery by way of a pipetting means (not shown), such as, but not limited to, a Finnpipette® from ThermoFisher Scientific of Waltham, Mass. The pipetted liquid is thus delivered to a lower platform 15, which is often configured as a pedestal or anvil-like surface that may include the end of a custom or commercial SMA fiber optic connector 16s, and of which, also may in some applications, be treated with a material known by those of ordinary skill in the art to prevent over spreading of the applied liquid drop analyte or reference sample (not shown).

Thereafter, upon the application of liquid drop, the apparatus 50, as now shown in FIG. 3A, is angularly moved by a user to be in the "closed position, so as to result in the upper pedestal or anvil-like surface 13, as specifically referenced in FIG. 3B, also often the end of a custom or commercial SMA fiber optic connector 12s, to be brought into contact with a dispensed liquid drop sample (not shown) to constrain a desired liquid drop sample therebetween with lower surface 15, also specifically referenced in FIG. 3B, in a surface tension mode.

As shown by the open position of FIG. 3B resulting in the closed position of FIG. 3A, such an angular movement of the swing arm 54 is enabled by the mechanical coupling of a hinge rod 56 configured therethrough bores in both the swing arm 54 and in the hinge spacer block 57, with hinge spacer block 57 being rigidly fixed with respect to base plate 52. Accordingly, the fiber optic connector 12s, which contains surface 13, and of which is mounted within and passes through a bore in swing arm 54, also angularly rotates with respect to a base plate 52 about hinge rod 56 in order to come into contact with a liquid drop sample dispensed on surface 15. A stop 53 coupled to the base plate 52 and which may be in the form of a pin provides a desired position against which the lower surface of the arm 54 abuts when the arm is rotated so as to provide for the contact and measurement of liquid drop sample.

As also illustrated in FIG. 3A and FIG. 3B, a pair of optical conduits, such as, for example, an upper optical fiber 18a and a lower optical fiber 18b and disposed within respective connectors, e.g., connectors 12s and 16s, enable optical communication by way of being diametrically opposed with one another in their operating position, i.e., the "closed position" illustrated in FIG. 3A.

It is to be noted that such optical conduits, e.g., optical fibers 18a and 18b, can be of any type, such as, single-mode fibers, polarization maintaining fibers, but preferably multi-mode fibers, so as to not constrain the present invention to any particular optical fiber measurement modality or limitation. As another example arrangement, the fiber ends are cleaved or polished and are often, but not necessarily, flush with the end of the fiber optic connector 12s and 16s. As another beneficial arrangement, such optical fibers 18a and 18b are coupled to one or more optical refractive surfaces (e.g. a lens (not shown)) additionally disposed within such fiber optical connectors 12s and 16s to provide for optical correction of the directed (e.g., collimation) and received (e.g., correction to the numerical aperture of the collection fiber) light so as to minimize deleterious optical losses between respective optical conduits 18a and 18b.

Turning now exclusively to FIG. 3A so as to describe the precise positioning of the surfaces 15 and 13 for measurement of a desired sample, it is to be noted that the lower optical fiber holder 16s for the lower optical fiber 18b also serves as a shaft for a linear actuator, as described in greater detail below. Although the upper optical fiber connector 12s (and consequently the coupled optical conduit fiber 18a) is fixed with respect to the swing arm 54, the lower optical fiber connector 16s (and consequently the lower optical conduit, e.g., fiber 18b) may translate, parallel to its axis (e.g., along the vertical direction), so as to enable the spacing between the two optical fibers to be varied. The base plate 52 is provided with a linear actuator that is mounted thereto so as provide for the precise translation of the lower optical fiber connector 16s. As shown in FIG. 3A, the linear actuator may include a motor 62 that is secured to the base plate 52 by means of fasteners 65 (such as, for instance, screws, posts, pins, rivets, etc. with or without associated bushings). The fasteners may also include extended motor mounting screws and may pass through bushings 68 which provide a slidable mechanical engagement with a plate or board 64, as further described below.

As generally illustrated in FIG. 3A, the motor is designed to produce a rotational motion of a threaded nut (not shown) which bears on a mating threaded shaft portion (not shown) of the lower optical fiber holder 16s. The lower fiber optic connector 16s replaces and/or serves as the actuator shaft of the linear actuator. The rotation of the internally threaded screw against the externally threaded shaft portion, as driven in either direction by the motor 62, causes controlled translation of the lower fiber optic connector 16s and the disposed optical conduit, e.g., 18b housed therein. The position of the lower fiber optic connector 16s may be stabilized by a plate or board 64 (e.g., a CPU board) which is mechanically coupled to the lower fiber optic holder 16s by means of an insert ring 66. The plate or board 64 may have holes or slots (not shown) through which the bushings 68 and the fasteners, such as screws 65, pass. The fasteners 65 may comprise extended motor mounting screws. The motor 62 may be further secured to the base plate 52 by additional fasteners (not shown).

As a beneficial arrangement, the motor 62 may be a commercially available motor or linear actuator or linear translator motor. As but one example, a linear actuator motor assembly is available from Haydon Switch Instruments of Waterbury Conn. USA as part no. 28H43-05-036. The actuator shaft of a standard off-the-shelf linear actuator or linear translator apparatus may need to be replaced by the lower fiber optic holder 16s, as described herein.

As a beneficial embodiment, the travel distance and/or position of the lower fiber optic holder 16s is monitored during operation of the apparatus 50, as shown in FIG. 3 so as to provide accurately measured path-lengths. As a beneficial configuration, the plate or board 64 may, in operation, be fixed to the lower fiber optic connector 16s, such that the plate or board moves together with the lower fiber optic holder. The plate or board 64 may comprise a printed circuit board (PCB) that carries electronics that perform the function of sensing movement or position of the plate or board 64. For example, the board 64 may carry a capacitance sensor, more often an eddy current sensor that can sense the distance of the board 64 to a back plate of the motor 62 configured with any material, such as, but not limited to, aluminum, steel, copper, magnetic materials, or in any other material that can induce an Eddy current so as to be sensed by the board of the present invention. Such Eddy current sensor PCB boards can be custom made or commercially available from a number of different manufacturers. Specifically, an Eddy current sensor PCB board 64 of the present invention often comprises a sensor coil (not shown), drive electronics (not shown) and a signal processing block (e.g., a circuit), also not shown. When such a configured sensor coil is driven by an AC current, it produces an oscillating field that induces Eddy currents in the plate configured on the motor 62. Such induced currents circulate in a path opposite to that of the coil positioned on the Eddy current sensor PCB board 64, which reduces the inductance and increases its resistance. In particular, movement of the board sensor with respect to the plate on motor 62 is reflected in an impedance change that is monitored so as to resolve micron-size displacements that enables path length measurements from about 1 mm down to about 5 microns accuracy.

The board 64 may also comprise a reference position sensor 82 that establishes a "home" or reference position when the motor control system initializes upon startup or interrupted by an opto-interrupter device 79' configured as part of a stop plate (See FIG. 5B, reference character 79) to enable interruption so as to provide not only a secondary stop mechanism but also as a home position. In addition, a collar or bushing 67 that is press fit onto a lowermost unthreaded portion of the lower fiber optic connector 16s, extending "underneath" the plate or board 64, may be added to act as a stop to prevent over-travel of the lower fiber optic holder 16s beyond its intended mechanical limits.

When the plate or board 64 is utilized as a position sensor, as described immediately above, the bushings 68 provide a slidable mechanical engagement between the holes or slots (not shown) of board 64 and the fasteners 65. Accordingly, such slots (not shown) and fasteners 65 permit translational movement of the board 64 (together with the lower fiber optic holder 16s) parallel to the axis of the lower fiber optic holder 16s but prevents rotation of the board and lower fiber optic holder with respect to the apparatus as a whole. Such rotation is undesirable as it could cause misalignment of, twisting of, light loss from or even breakage of the optical fiber contained within the lower fiber optic holder 16s.

The insert ring 66 may be either permanently or temporarily fastened to the plate or board 64. For instance, the insert ring may be permanently fastened to the plate or board with solder. Likewise, the insert ring 66 may be either permanently or temporarily fastened to the lower fiber optic holder 16s by known techniques understood by those of ordinary skill in the art. If, in operation, the lower fiber optic holder 16s and plate or board 64 moves in unison, then the insert ring 66 is coupled to both the lower fiber optic holder 16s and the plate or board 64 at least during such operation. In order to facilitate assembly or replacement of parts, it may be desirable to employ a non-permanent coupling between the lower fiber optic holder 16s and the insert ring 66, such that the lower fiber optic holder may, on occasion, be removed from the rest of the apparatus. The non-permanent fastening may include a tightly locked mechanical engagement between the external threads of the threaded portion (not shown) of the lower fiber optic holder 16s and internal threads of an inner hollow portion of the insert ring 66. In such a fashion, the lower fiber optic holder 16s may be held sufficiently tight in the insert ring such that it does not rotate during operation of the motor 62, yet may still be easily disengaged from the insert ring during dis-assembly.

Upon proper positioning of the surfaces 13 and 15, as shown in FIG. 3B, via the motor controlled mechanism(s) and sensor(s) described above, and wherein a sample column is drawn in the surface-tension-mode, light is then directed through, for example, fiber optic 18a or other conventional optical means so as to be further directed through connector 12s, a sample 14, as shown in FIGS. 1A-2B, and thereafter accordingly received by fiber optic 18b. The optical light is then selected for analysis so as to be thereafter coupled to a detection master commercial or custom made spectrometer (not shown).

A light source (not shown) of the present invention for interrogation comprises a radiation source, such as, a xenon flash lamp or a combined deuterium arc and quartz halogen incandescent lamp commercially available from Ocean Optics, inc. p/n DT-1000). While such a commercially available source is beneficial, it is also to be understood that any source capable of delivering illumination wavelengths of at least about 200 nm, more often illumination wavelengths of between about 190 nm up to about 840 nm can also be utilized in the present invention when conformed to the design parameters of the present invention. In addition, depending on the light source utilized and the measurement to be made, filters such as an interference filter, can be applied so as to permit desired wavelengths of between about 190 nm up to about 840 nm. If desired, can be formed into a cartridge or wheel format (not shown) to permit the ready insertion or withdrawal of such filter from designed regions of the optical path.

Moreover, the spectrometer (not shown), light source, (not shown), motor driven mechanisms, etc., are coupled to a computer driven (PC) system (not shown) having sophisticated custom or commercial software, with in some cases pre-programmed modules for common functions like DNA, RNA, and protein quantification. The data acquired can be displayed via known methods and stored for future reference, and statistical measures performed to enable a user friendly operation. As another arrangement, the software may be built in to the spectrometer as opposed to the PC. As another beneficial arrangement, data can be exported to a portable storage device such as a flash drive, or even directly to a PC through a USB or wireless (Bluetooth), IEEE, Ultra-Wideband (UWB) connection.

Accordingly, the apparatus of FIGS. 3A and 3B enable a user in the surface-tension-mode to precisely control separation between an upper fiber (or other optical component) and a lower fiber (or other optical component) in order to make controlled optical absorption measurements of small quantity liquid drop analyte samples of less than about 10 µl, more often less than about 2 µl, having a path length of down to about 10µ, more often down to about 10µ, without the need for mechanical movement of bulky supporting parts or without the need for large sample volumes that may require dilution and cuvettes when applicable.

Figure 4:
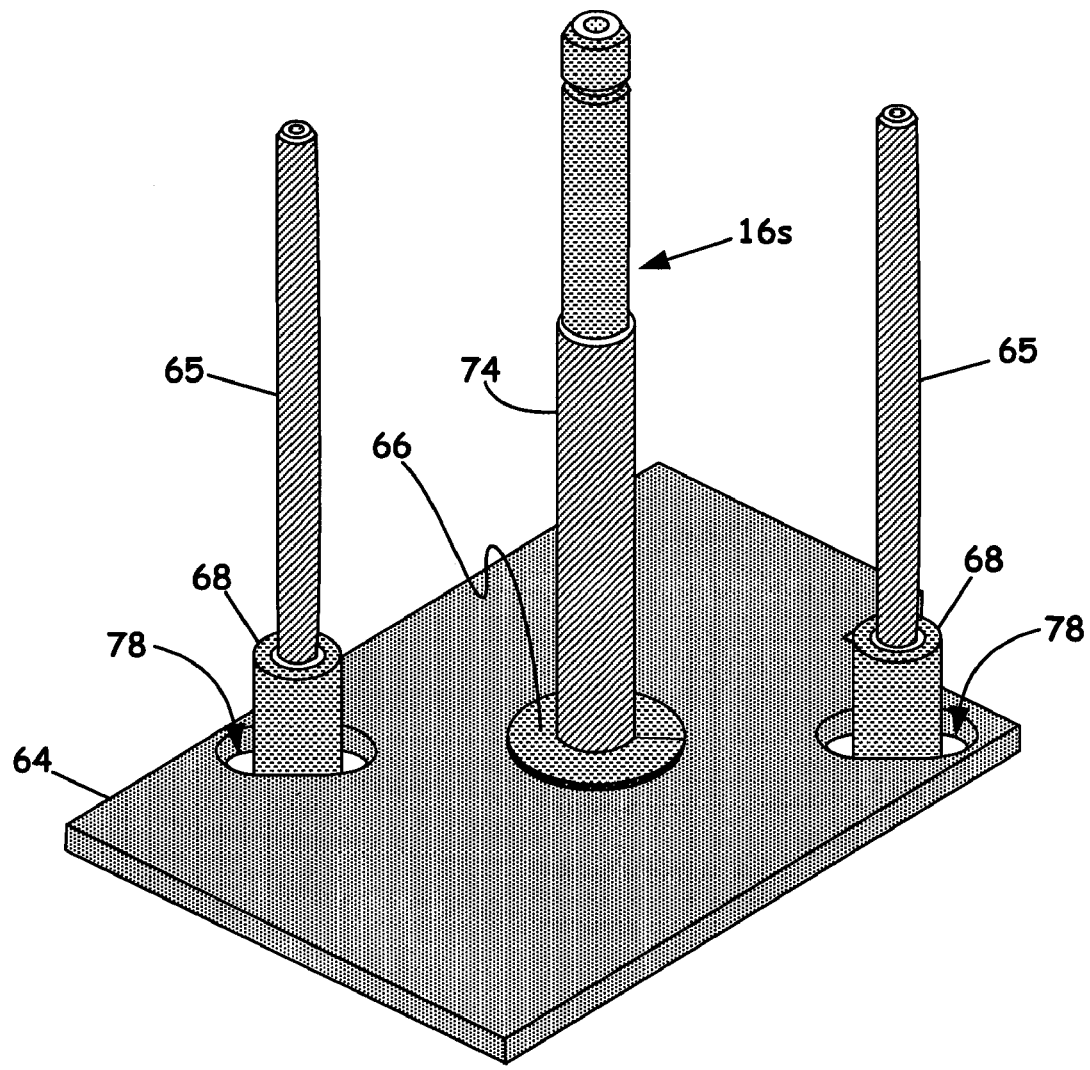
FIG. 4 is a perspective view of a fiber optic holder comprising a threaded hollow screw, and an associated plate or board in accordance with embodiments of the present invention.

FIG. 4 shows a more detailed perspective view of the lower fiber optic holder 16s as well as an associated mounting plate in accordance with some embodiments of the invention. In the example configuration shown in FIG. 4, the motor produces a rotational motion of a threaded nut (not shown) which bears on a mating threaded shaft portion 74 of the lower optical fiber holder 16s. The lower fiber optic holder replaces and/or serves as the actuator shaft of the linear actuator. The rotation of the internally threaded screw against the externally threaded shaft portion 74, as driven in either direction by the motor 62, as shown in FIGS. 3A and 3B, causes controlled translation of the lower fiber optic holder 16s and the lower fiber 18b housed therein. The position of the lower fiber optic holder may be stabilized by a plate or board 64 (FIGS. 3A-3B) which is mechanically coupled to the lower fiber optic holder 16s by means of an insert ring 66. The plate or board 64 may have holes or slots 78 (as shown in FIG. 4) through which the bushings 68 and the fasteners, such as screws 65, pass. The fasteners 65 may comprise extended motor mounting screws. The motor 62, as shown in FIGS. 3A and 3B, may be further secured to the base plate 52, also as shown in FIGS. 3A and 3B, by additional fasteners (not shown).

Often, the travel distance and/or position of the lower fiber optic holder 16s is monitored during operation of the apparatus 50 (FIGS. 3A-3B), as described above, for example, by the Eddy current sensor aspect. Beneficially, the plate or board 64 may, in operation, be fixed to the lower fiber optic holder, such that the plate or board moves together with the lower fiber optic holder. The plate or board 64 may comprise a printed circuit board (PCB) that carries electronics that perform the function of sensing movement or position (e.g., using an Eddy current sensor) of the plate or board 64.

When the plate or board 64 is utilized as a position sensor, as described immediately above, the bushings 68 provide a slidable mechanical engagement between the holes or slots 78 of board 64 and the fasteners 65 that permits translational movement of the board 64 (together with the lower fiber optic holder 16s) parallel to the axis of the lower fiber optic holder 16s but that prevents rotation of the board and lower fiber optic holder with respect to the apparatus as a whole. Such rotation is undesirable as it could cause misalignment of, twisting of, light loss from or even breakage of the optical fiber contained within the lower fiber optic holder 16s.

The insert ring 66 may be either permanently or temporarily coupled to the plate or board 64. For instance, the insert ring may be permanently coupled to the plate or board with solder. Likewise, the insert ring 66 may be either permanently or temporarily coupled to the lower fiber optic holder 16s. If in operation, the lower fiber optic holder 16s and the plate or board 64 moves in unison, as previously described, then the insert ring 66 is fastened to both the lower fiber optic holder 16s and the plate or board 64 at least during such operation. In order to facilitate assembly or replacement of parts, it may be desirable to employ a non-permanent fastening between the lower fiber optic holder 16s and the insert ring 66, such that the lower fiber optic holder may, on occasion, be removed from the rest of the apparatus. The non-permanent fastening may include a tightly locked mechanical engagement between the external threads of the threaded portion 74 of the lower fiber optic holder 16s and internal threads of an inner hollow portion of the insert ring 66. In this fashion, the lower fiber optic holder may be held sufficiently tight in the insert ring such that it does not rotate during operation of the motor 62, yet may still be easily disengaged from the insert ring during disassembly.

Figure 5A:
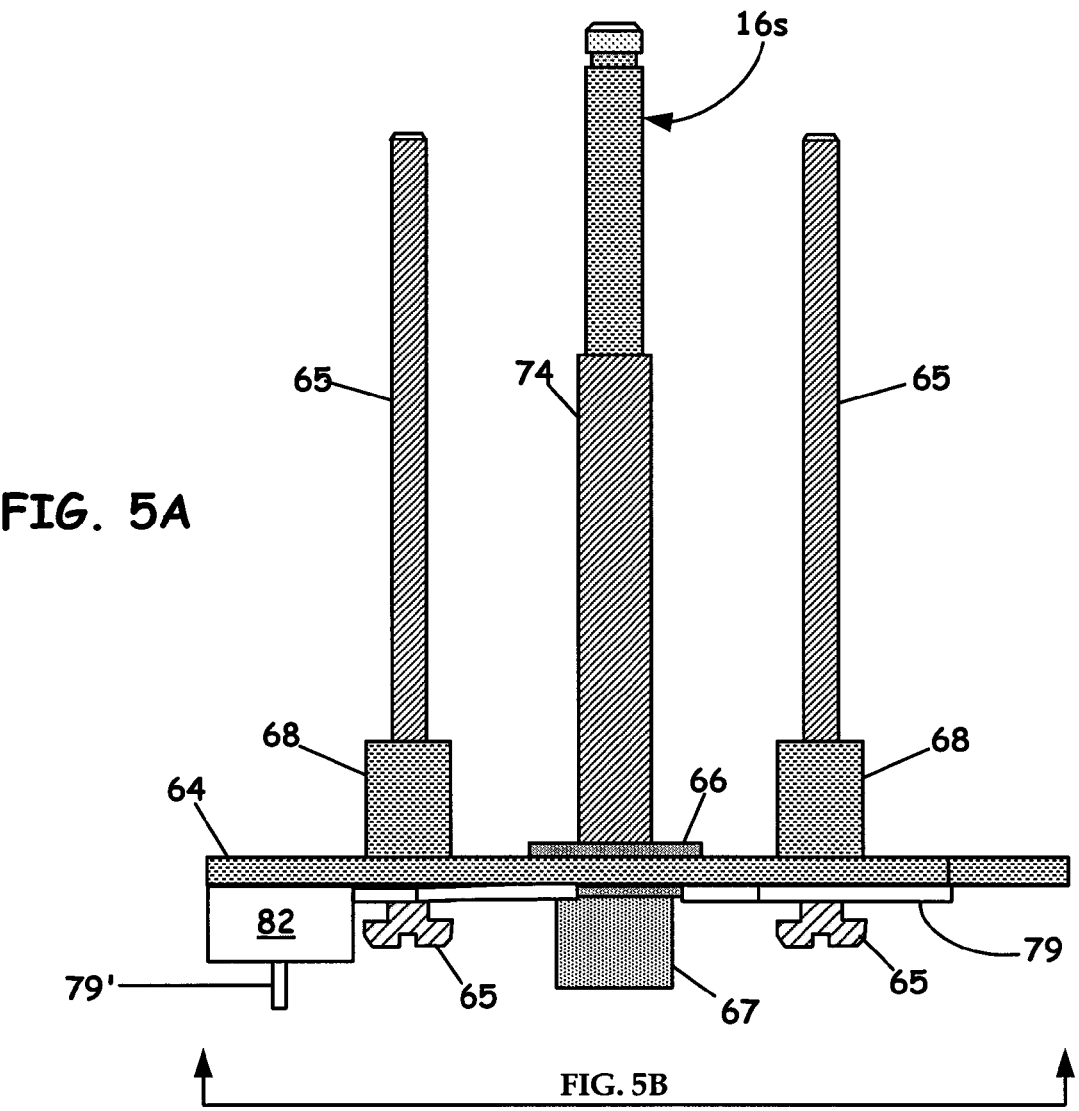
FIG. 5A shows a view of the fiber optic holder and plate or board of FIG. 4 illustrating the fiber optic holder and plate or board disposed in a lower range position.
Figure 5B:
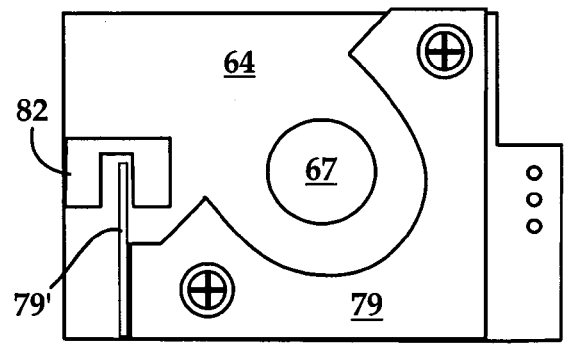
FIG. 5B shows the fiber optic holder and plate or board coupled to the optical interrupter and optical sensor from an underneath perspective.
Figure 5C:
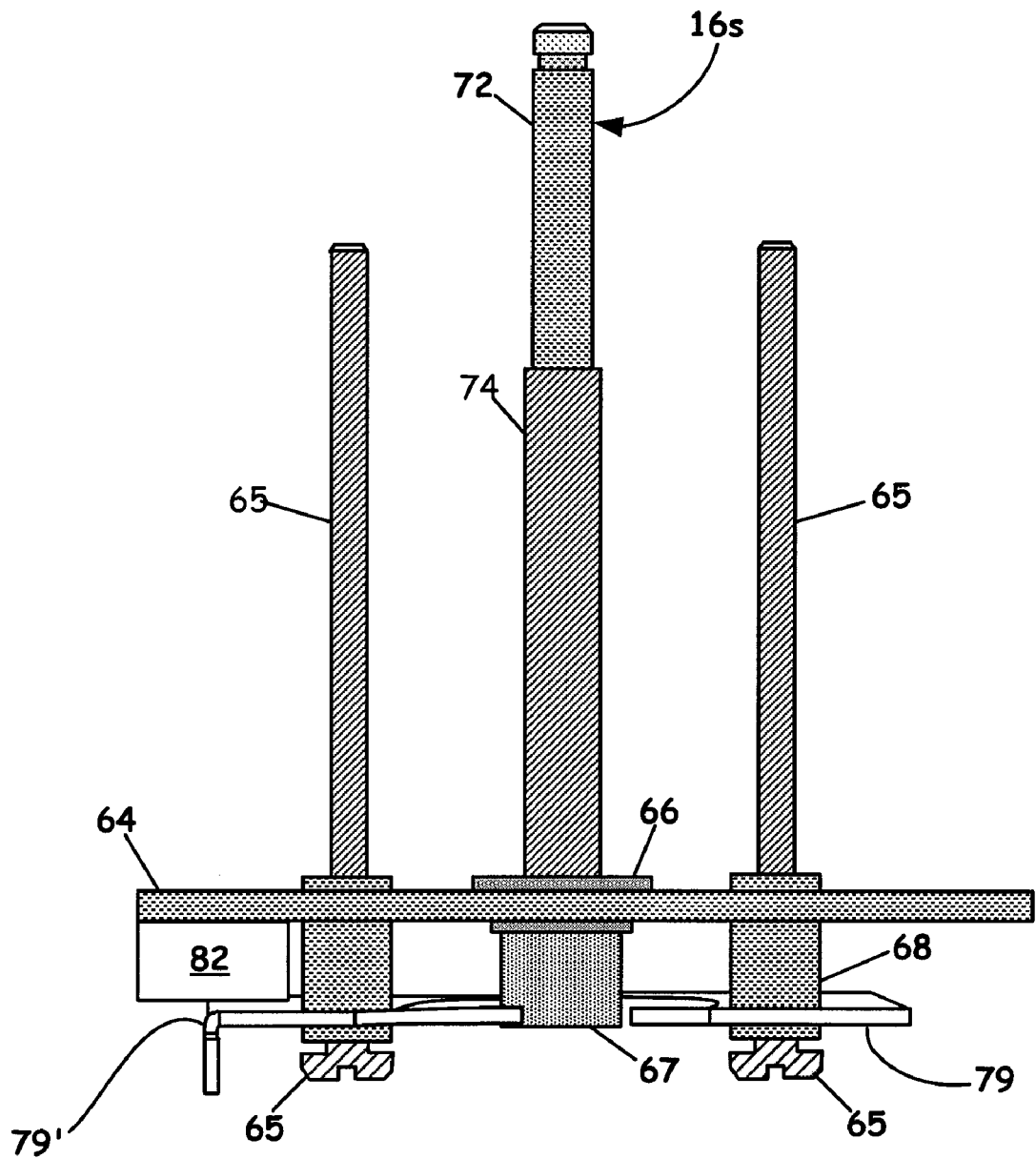
FIG. 5C shows a view of the fiber optic holder and plate or board of FIG. 4 illustrating the fiber optic holder and plate or board disposed in an upper range position.

FIGS. 5A and 5C show elevation views of the fiber optic holder 16s and plate or board 64. These elevation views show a collar or bushing 67 that is press fit onto a lowermost unthreaded portion of the lower fiber optic holder extending "underneath" the plate or board 64, i.e., the side of the board opposite to the motor. The collar or bushing 67 may act as a stop to prevent over-travel of the lower fiber optic holder beyond its intended mechanical limits. Additionally, a stop plate 79 (FIG. 5C) with a portion configured as an opto-interrupter device 79' to enable interruption via an optical sensor 82, can also beneficially be configured with the apparatus depicted in 5A and 5C so as to provide not only a secondary stop mechanism but also as a home position. FIG. 5A shows the lower fiber optic holder 16s, insert ring 66, plate or board 64 and collar or bushing 67 as fastened and moving in unison, with FIG. 5A and FIG. 5C respectively showing these parts at a lower range and at an upper range of their travel.

FIG. 5B show a bottom view of the collar or bushing 67, stop plate 79 having a configured opto-interrupter device 79' in working combination with optical sensor 82, all as coupled to the board 64, of the present invention.

Figure 6A:
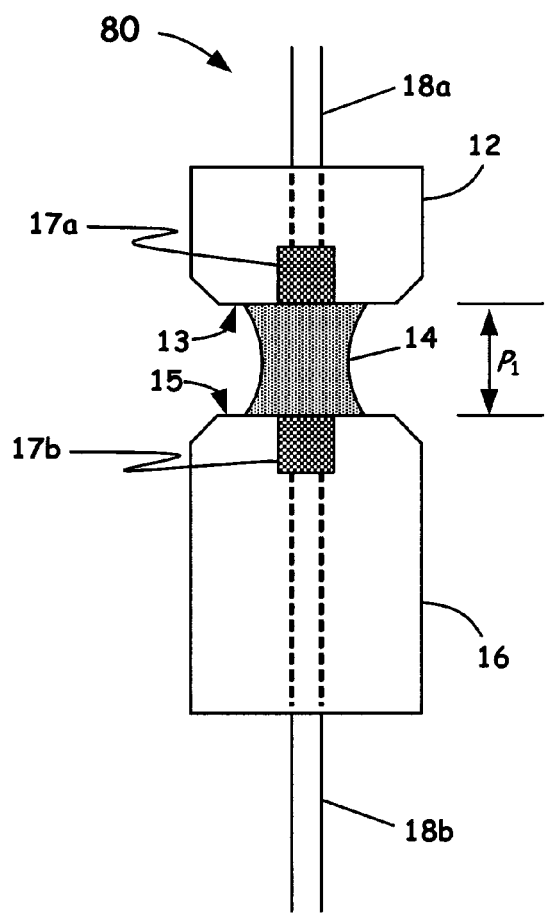
FIGS. 6A and 6B are two views of an alternative embodiment of an apparatus, in accordance with the invention, for measuring absorbance through a liquid sample maintained between two surfaces by interfacial tension.
Figure 6B:
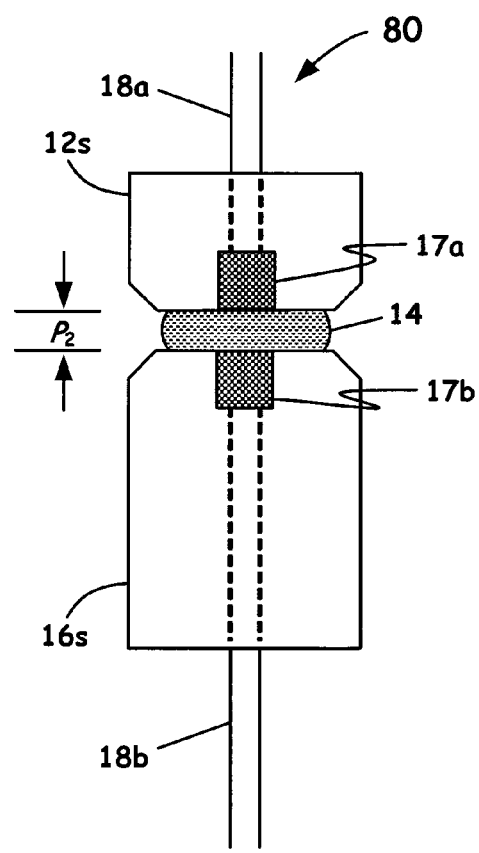

FIGS. 6A-6B are two views of an alternative embodiment of an apparatus, in accordance with the invention, for measuring absorbance through a liquid sample maintained between two surfaces by interfacial tension. In the embodiments described earlier in the present invention (for instance, FIGS. 2A-2B), the fibers may be finished and polished flush with the upper and lower anvils or pedestals. However, in the alternative embodiment 80 shown in FIGS. 6A-6B, the fibers 18a-18b do not pass all the way through the anvils or pedestals to the respective surfaces 13 and 15. Instead, a lens may be embedded in one or the other of the anvils or pedestals in order to either collimate light entering the sample or efficiently collect light from the sample. For example, if light is provided by the lower fiber 18b, then this light is collimated by lens 17b after emerging from fiber 18b and prior to entering the sample 14. Any light transmitted through the sample is then collected by lens 17a and focused into the end of fiber 18a for delivery to a detector (not shown). As example configurations, the lenses 17a-17b may be custom or commercial graded-index (GRIN) lenses, the exposed flat surfaces of which may be disposed flush with surface 13 and surface 15, respectively.

Figure 7:
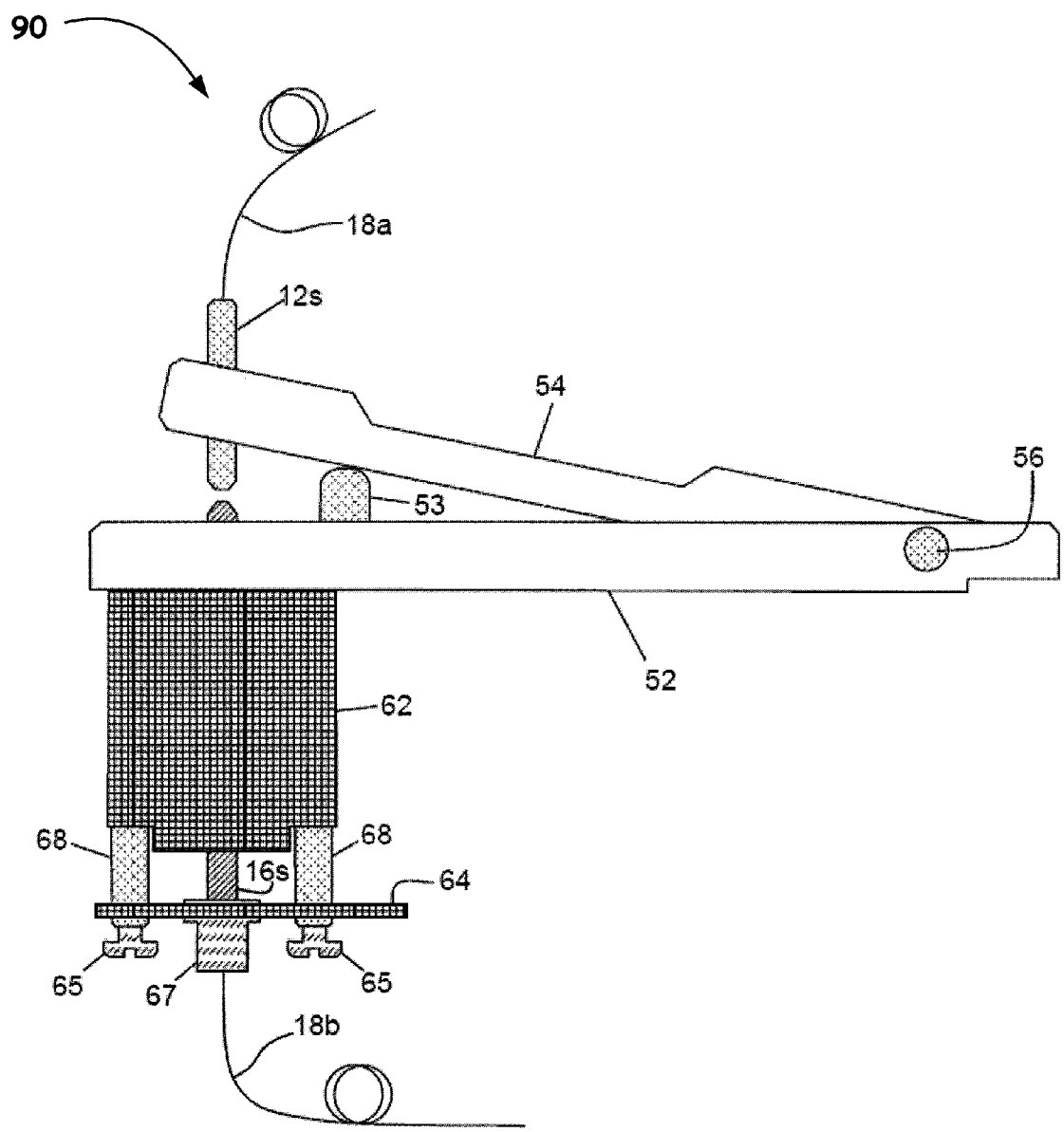
FIG. 7 shows a side view of an apparatus in accordance with an alternative beneficial configuration of the present invention.

FIG. 7 is a side view of in apparatus in accordance with an alternative embodiment of the invention. All common reference numerals are the same as previously utilized. In the apparatus 90 shown in FIG. 7, the hinge spacer block is removed. Instead, the hinge rod 56 passes through both the base plate and the arm 54. Since the hinge rod defines the axis of rotation of the arm 54, the arm does not reside parallel to the base plate 52 at the stop position when the arm 54 abuts against the mechanical stop 53. However, the upper fiber optic holder 12s nonetheless still comes to a stop position such that a length of the upper fiber 18a within the upper fiber optic holder 12s is coaxial with a length of the lower fiber 18b within the lower fiber optic holder. The disposition of the upper fiber optic holder 12s with respect to the arm 54 thus assures that the fibers are optically aligned with respect to one another at the stop position.

Figure 8:
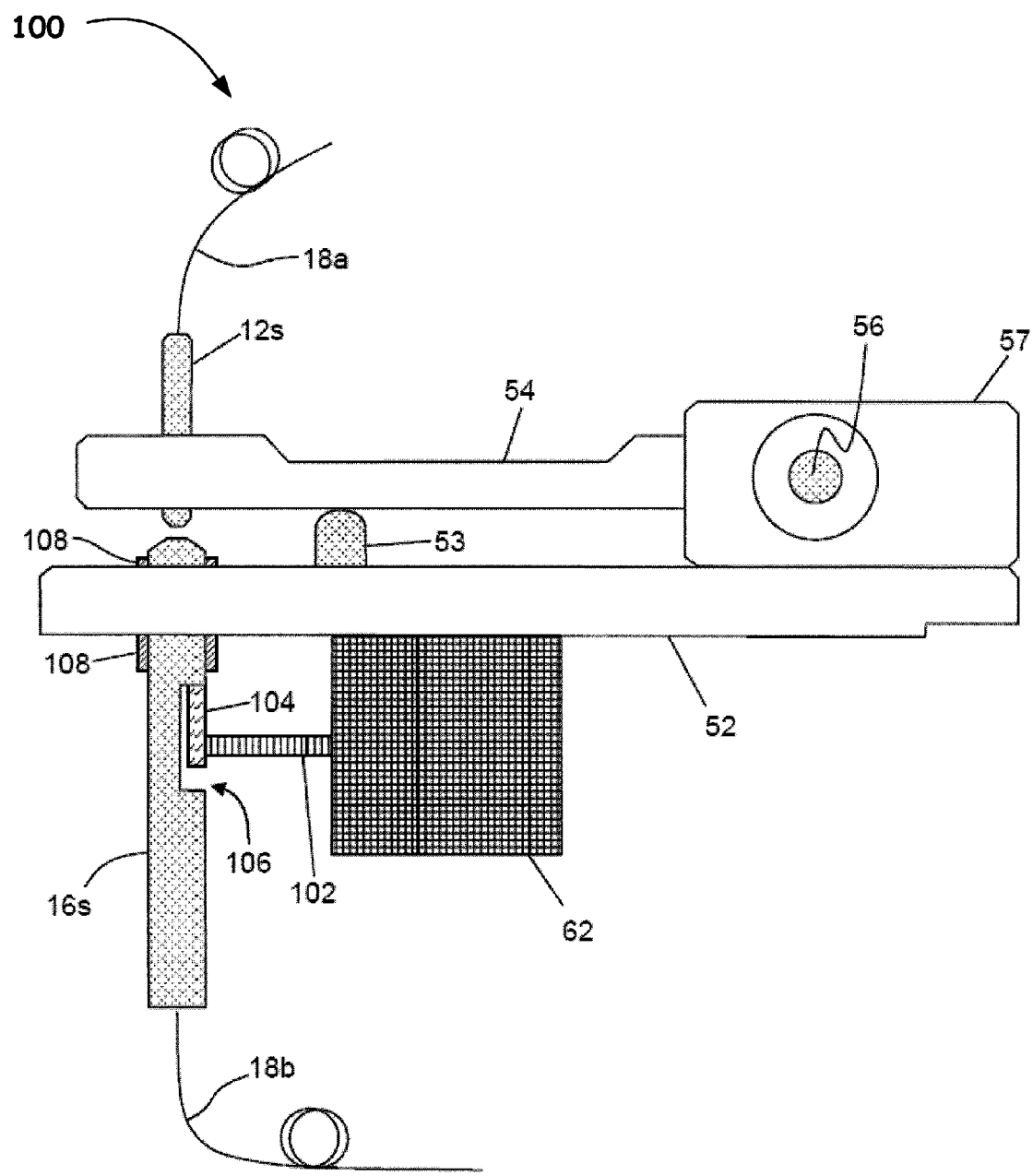
FIG. 8 shows a side view of an apparatus in accordance with an additional beneficial configuration of the present invention.

FIG. 8 is a side view of an apparatus in accordance with another alternative embodiment of the invention. All common reference numerals are the same as previously utilized. In the apparatus 100 shown in FIG. 8, the lower fiber optic holder 16s is driven directly from a cam 104 (or other means) rotated by a camshaft 102 that is rotated by a motor 62. Such an arrangement is able to translate rotational motion into linear motion. The cam 104 may engage against a wall of a slot or recess 106 of the lower fiber optic holder 16s. Preferably, means to assure proper loading of the lower fiber optic holder are provided, such as a spring and bearings constraining the radial position of a bushing 108 enveloping the lower fiber optic holder at its passage through the base plate 52. Such bearings could be simple sapphire journal bearings or a linear ball bearing.

Figure 9:
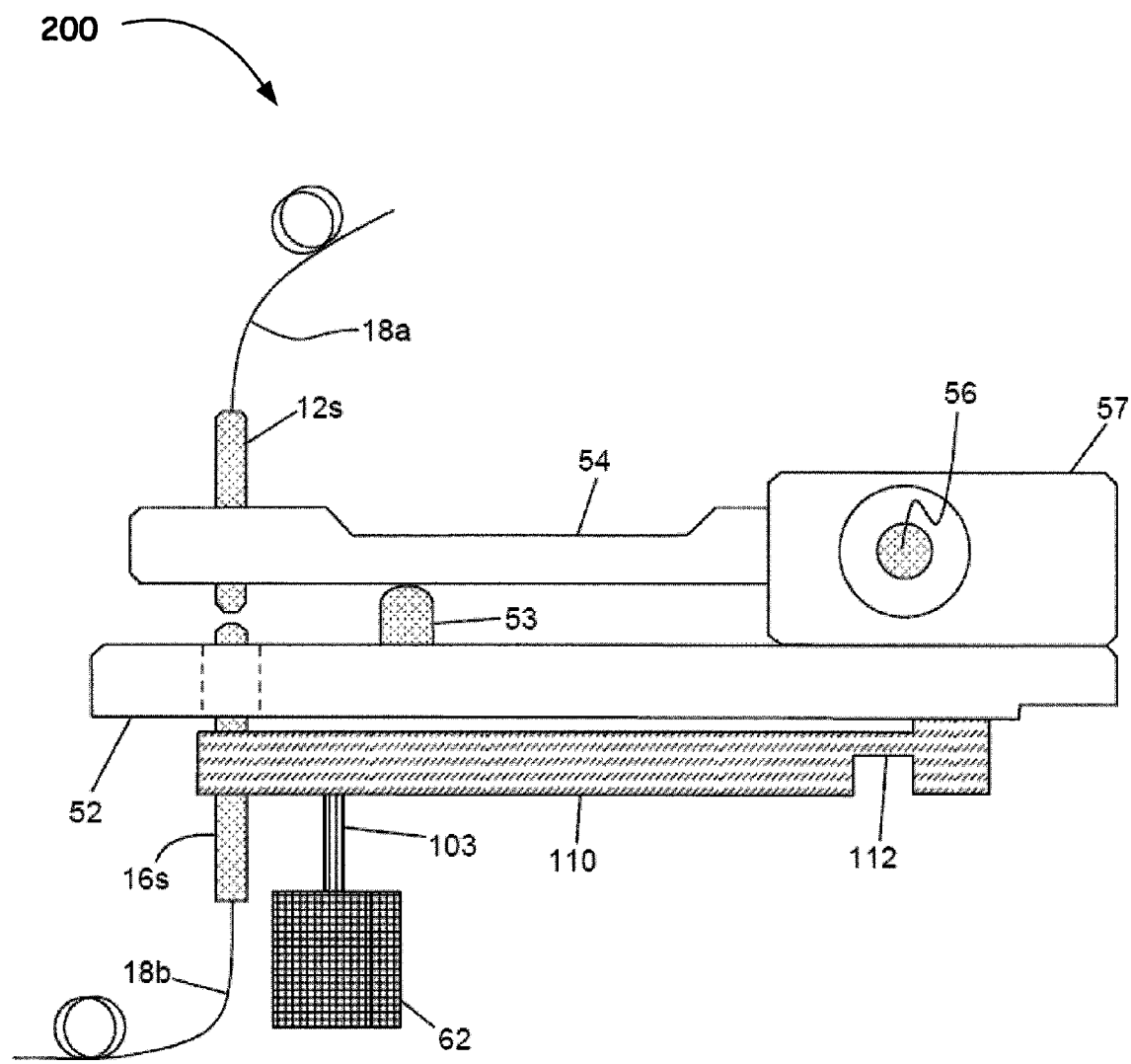
FIG. 9 shows a side view of an apparatus in accordance with yet another alternative beneficial configuration of the present invention.

FIG. 9 is a side view of an apparatus in accordance with still another alternative embodiment of the invention. All common reference numerals are the same as previously utilized. In the apparatus generally designated by the reference numeral 200, as shown in FIG. 9, the lower fiber optic holder 16s is not directly coupled to the base plate 52. Instead, the lower fiber optic holder 16s mechanically coupled to an auxiliary base plate 110 that is capable of flexing at a flexure bearing 112 that may include a thinned region of the auxiliary base plate. The auxiliary base plate 110 is mounted to the base plate 52 on the opposite side of the flexure bearing from the attachment of the lower fiber optic holder, leaving a length of the auxiliary base plate free to flex, thereby driving movement of the attached lower fiber optic holder. Such flexure is controlled by a motor 62 that that operates a linear actuator shaft 103 that bears against the auxiliary base plate.

Accordingly, the configurations described above enable precisely controlled separation between an upper fiber (or other optical component) and a lower fiber (or other optical component) in order to make controlled optical absorption measurements of a small quantity (e.g., a droplet) of a sample without the need for mechanical movement of bulky supporting parts, such as a base plate, arm or apparatus body. Beneficially, since only one fiber optic holder (and the fiber contained therein) moves during such controlled separation and since, the fiber optic holder may, in fact, comprise a shaft of a linear actuator, the number ancillary parts and possible associated unwanted motions are maintained at a minimum. Conveniently, the moveable fiber optic holder may be a replacement for or perhaps, a modification of, an existing linear actuator shaft in order to simplify fabrication. The moveable fiber optic holder may be attached to a plate or board, which may be a position sensor printed circuit board, which moves together with the moveable fiber optic holder. One or more bushings that are slidably mechanically engaged to the plate or board permit motion of the fiber optic holder parallel to its axis but prevent unwanted side-to-side or rotational motions which could adversely affect optical alignment or even cause fiber breakage.

With respect to the actual measurement itself, the quantity generally obtained in an absorption spectrum is relative transmission (T), given by $T=I_R(\lambda)/I_0(\lambda) \equiv (I_R/I_0)(\lambda)$ where $I_R(\lambda)$ is the measured intensity (i.e., power) of light transmitted through a sample and $I_0(\lambda)$ is a reference intensity, generally taken with no sample present. The usual quantity of interest, however, is absorbance, A, as given by Eq. 1. Let A be considered as a function of $I_R$, that is, let $A \equiv f(I_R)$, and let the experimental measurement obtained at each wavelength, $\lambda$, be represented as a sum of the non-random variable, $I_{actual}(\lambda)$, and two random variables $X_{RMS}(\lambda)$ and $X_{1/f}$. Thus, according to this representation, $$a.\ I_R(\lambda) = I_{actual}(\lambda) + X_{RMS}(\lambda) + X_{1/f} \qquad \text{Eq. 4}$$

in which $I_{actual}$ is the hypothetical actual or true value of light intensity reaching the detector and detectable thereby, $X_{RMS}$ is the so-called shot noise and $X_{1/f}$ is system noise (e.g., "1/f noise") that is not dependent upon signal level. The variance of the shot noise is given as by the square root of $I_{actual}$, whereas the variance of the system noise is a constant, k, independent of $I_R$ (or $I_{actual}$). The statistical expectation value, $E(I_R)$, of the quantity $I_R$ is given simply as $E(I_R) = I_{actual}$. Further, the variance of the non-random variable $I_{actual}$ is equal to zero and $I_0$ is a simple constant at each $\lambda$ (but not necessarily the same constant for all $\lambda$). Since the two random variables $X_{RMS}$ and $X_{1/f}$ are independent of one another, their covariance is nil, that is, $Cov(X_{RMS}, X_{1/f}) = 0$. Thus, $$b.\ Var(I_R) = Var(X_{RMS} + X_{1/f}) = Var(X_{RMS}) + Var(X_{1/f}). \qquad \text{Eq. 5a}$$

or, in an alternative form, $$c.\ Var(T) = (1/I_0^2) Var(I_R) = (1/I_0^2) Var(X_{RMS}) + (1/I_0^2) Var(X_{1/f}) \qquad \text{Eq. 5b}$$

Although the above random variables are given as functions or $I_R$ and T, it is desirable to calculate signal-to-noise ratio in terms of absorbance, A, which is a function of $I_R$ as given by Eq. 1. The variance of the function, $f$, of the random variable $I_R$ may be approximated as follows:

$$Var[A] = Var[f(T)] \qquad \text{Eq. 6}$$
$$\approx (f'(E[T]))^2 Var[T]$$
$$= \left(\frac{(\ln 10)^2}{T_{actual}^2}\right)\left(\frac{(I_{actual}^{1/2} + k)}{I_0^2}\right).$$

The expected signal-to-noise ratio (S/N), in terms of absorbance, may thus be represented as:

$$S/N = \frac{A}{Var[A]} = \frac{AI_0^2}{(\ln 10)^2 \times 10^{2A}[I_0^{1/2} 10^{-A/2} + k]}. \qquad \text{Eq. 7}$$

Figure 10A:
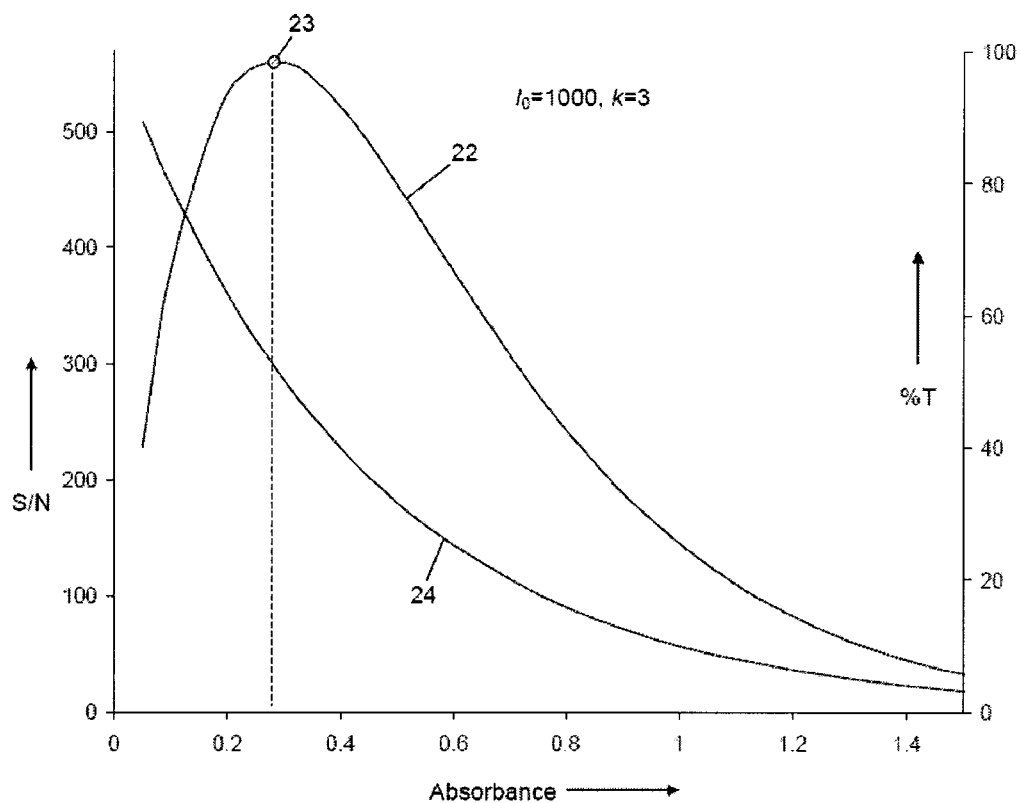
FIGS. 10A and 10B illustrate graphs of percentage transmission and calculated signal-to-noise ratios for different combinations of values of reference intensity, $I_0$, and system noise variance, k.
Figure 10B:
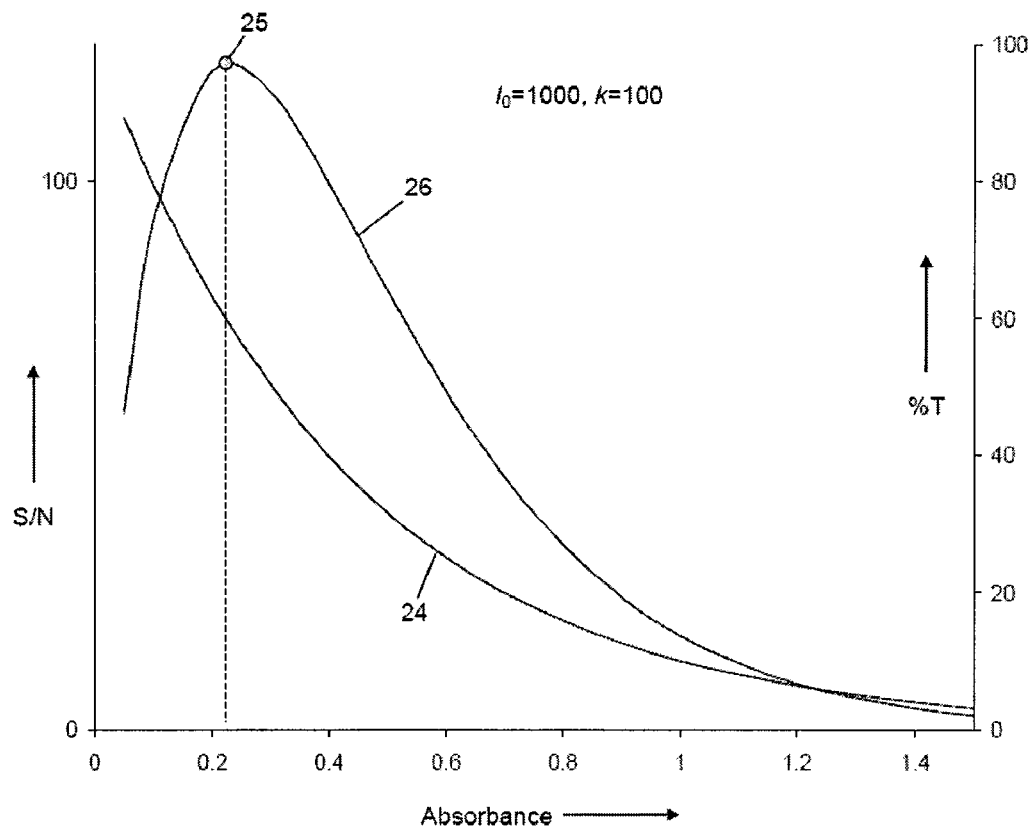

FIGS. 10A and 10B are graphs of percentage transmission signal-to-noise ratio calculated according to Eq. 7. On these graphs, absorbance is plotted as the abscissa and calculated signal-to-noise ratio (S/N) and percentage transmission (% T) are plotted on two different ordinate scales, respectively shown along the leftmost and rightmost vertical axes of the graphs. Curve 24, representing percentage transmission, % T, is the same curve in both FIG. 10A and FIG. 10B since the absorbance scale is identical in both graphs and % T is a single valued function of A.

Curve 22 with a peak 23 in FIG. 10A is the calculated S/N using arbitrary units of $I_0=1000$ and $k=3$ in the formulation of Eq. 7. Likewise, curve 26 with a peak 25 in FIG. 10B is the calculated S/N using arbitrary units of $I_0=1000$ and $k=100$. Comparison between curve 22 (FIG. 10A) and curve 26 (FIG. 10B) illustrates that an increase in system background noise (with constant $I_0$) both decreases the overall absorbance signal-to-noise ratio and shifts the S/N maximum to lower values of absorbance (greater $I_R$), as expected. It is been found that the optimal range for absorbance, A, is approximately 0.3-0.7, with the best S/N characteristics at an absorbance value of 0.43.

Figure 1B:
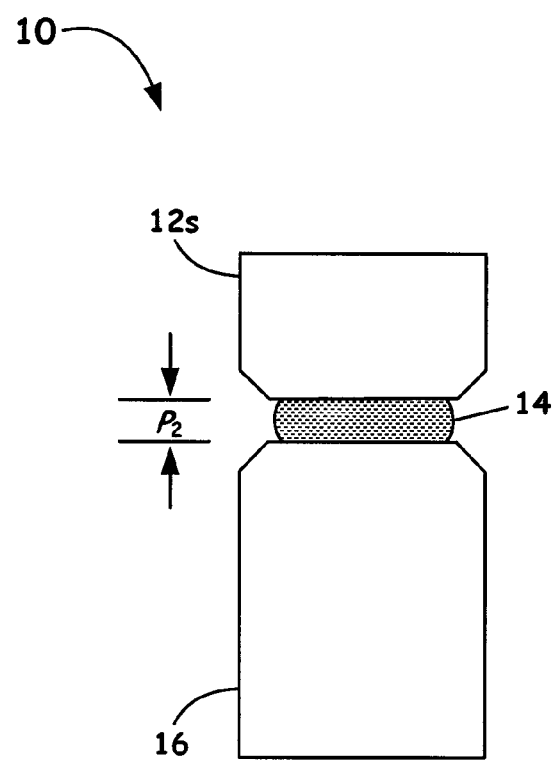

By inputting data appropriate to their own system and sample, a user may use Eq. 3 or graphs such as shown in FIGS. 10A and 10B, in accordance with a method embodiment of the invention, as a guide to setting a light path length through a sample so as to obtain improved or optimal signal-to-noise characteristics. For instance, in many situations, an apparatus such as apparatus 10, as shown in FIGS. 1A and 1B, may be used to detect the presence of an analyte in a liquid sample at or above some pre-defined minimum concentration.

Both $\epsilon$ and A in Eq. 3 will, in general, be functions of $\lambda$. For any given target analyte, the value of absorptivity, e, will often be known beforehand, either through consultation of standard tables or a standard database or by a pre-experiment comprising accurate measurement of a concentrated or neat sample of the analyte. Thus, for instance, a user may set the value of P, using apparatus 10 (FIGS. 1A-1B) and the results of Eq. 7, so as to yield the best possible signal-to-noise for an optical absorption measurement for the purpose of determining an analyte concentration, c.

As stated above, the optimal range for absorbance, A, is approximately 0.3-0.7, with the best S/N characteristics at an absorbance value of 0.43. In particular, as an alternative to the rigorous derivations as shown above, the usual quantity of interest, i.e., absorbance, A, as given by Eq. 3, can also be generally expressed as:

$$A = 2 - \log T \quad \text{Eq. 8;}$$

where A is the absorbance and T is the percent transmission of the of the radiation.

Figure 10C:
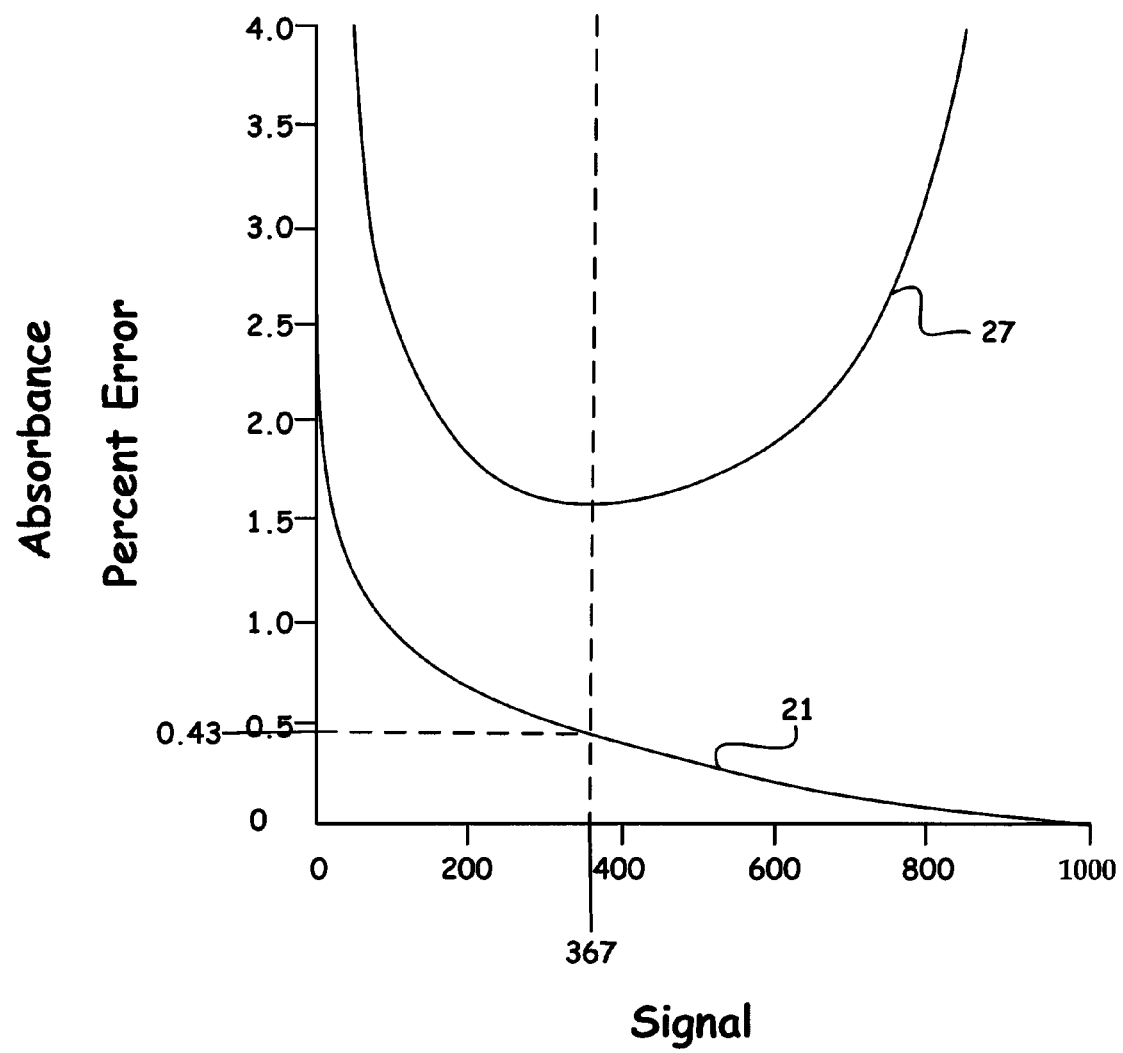
FIG. 10C shows a graph of transmitted signal intensity on the horizontal axis versus absorbance and percent error on the vertical axis for an example signal of 1000 with no sample present.

FIG. 10C illustrates the concept via a graph of example data which shows transmitted signal intensity on the horizontal axis versus absorbance and percent error on the vertical axis for an example signal of 1000 with no sample present. Accordingly, the absorbance 21 for such an arrangement is shown in the lower plot and the percent error 27, having an assumed fixed noise component set here to +/−3 units of signal, is shown by the upper plot of FIG. 10C. As shown, the error minimum occurs in the data at an absorbance of approximately 0.43, where the signal is 1/e times the unabsorbed signal with e being the natural logarithm.

Therefore, in reference back to FIGS. 1A-2B, because absorbance is linearly related to sample thickness having units of $cm^{-1}$, if a user sets the sample thickness $P_1$-$P_2$, such that the sample absorbance is about 0.43, the sample absorbance in $cm^{-1}$ can be calculated by dividing 1 cm by the sample pathlength and multiplying the result by, for example, 0.43, i.e.:

$$\text{Absorbance }(A) = 0.43 \times (1/P), \quad \text{Eq. 9;}$$

where P is the set sample pathlength in cm.

Accordingly, as an example method of operation, if the pathlength through the sample is set so that the sample absorbance is, for example, 0.43, then under commonly encountered conditions the effects of noise on the measurement is minimized.

Figure 11:
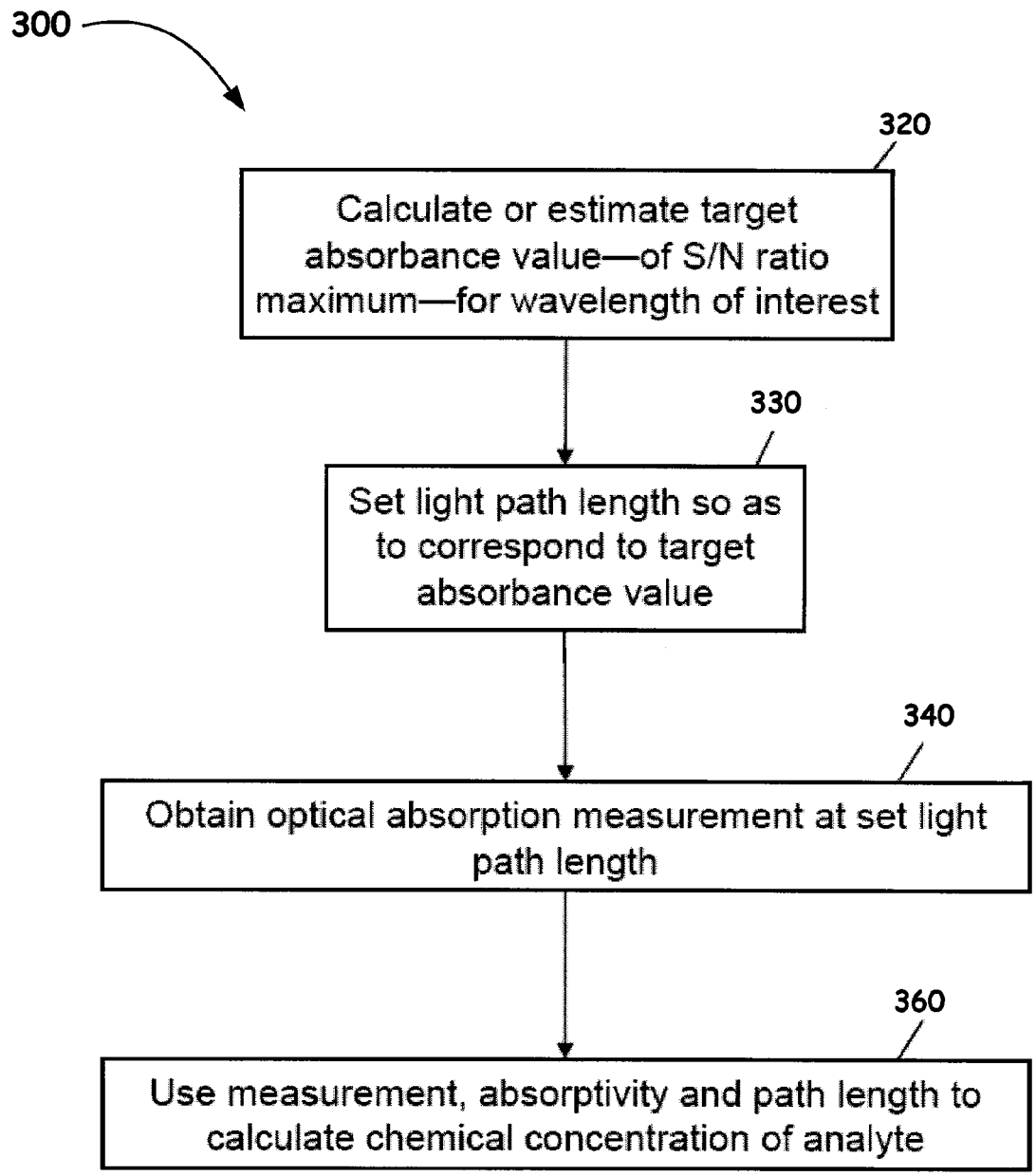
FIG. 11 is a flowchart of a first exemplary method in accordance with an embodiment of the invention.

These steps are outlined in method 300, shown in FIG. 11. Accordingly, in step 320 of method 300, a target absorbance value is calculated or estimated, possibly for a wavelength of interest that will yield the most favorable S/N. Generally, the wavelength of interest may be a known absorption line or band of a target analyte. Then, in step 330, a light path length is set so as to correspond to target absorbance value using, for instance, Eq. 8, or a similar representation as discussed above. In step 340, an optical absorption measurement is obtained at the set path length and, finally, in step 360, this measurement is converted to concentration of the analyte in conjunction with the known absorptivity and set path length (e.g., see Eq. 3). A similar procedure can be used to determine $\epsilon$, if c is known.

In some experimental situations, it may be desirable to perform a preliminary rough scan of A versus P so as to determine a value of P which will yield the best signal-to-noise ratio for a subsequent careful measurement of A. Details of an exemplary method, method 400, in accordance with an embodiment of the invention, for performing such operations are shown in FIG. 12 and discussed in greater detail in the following discussion.

Figure 12:
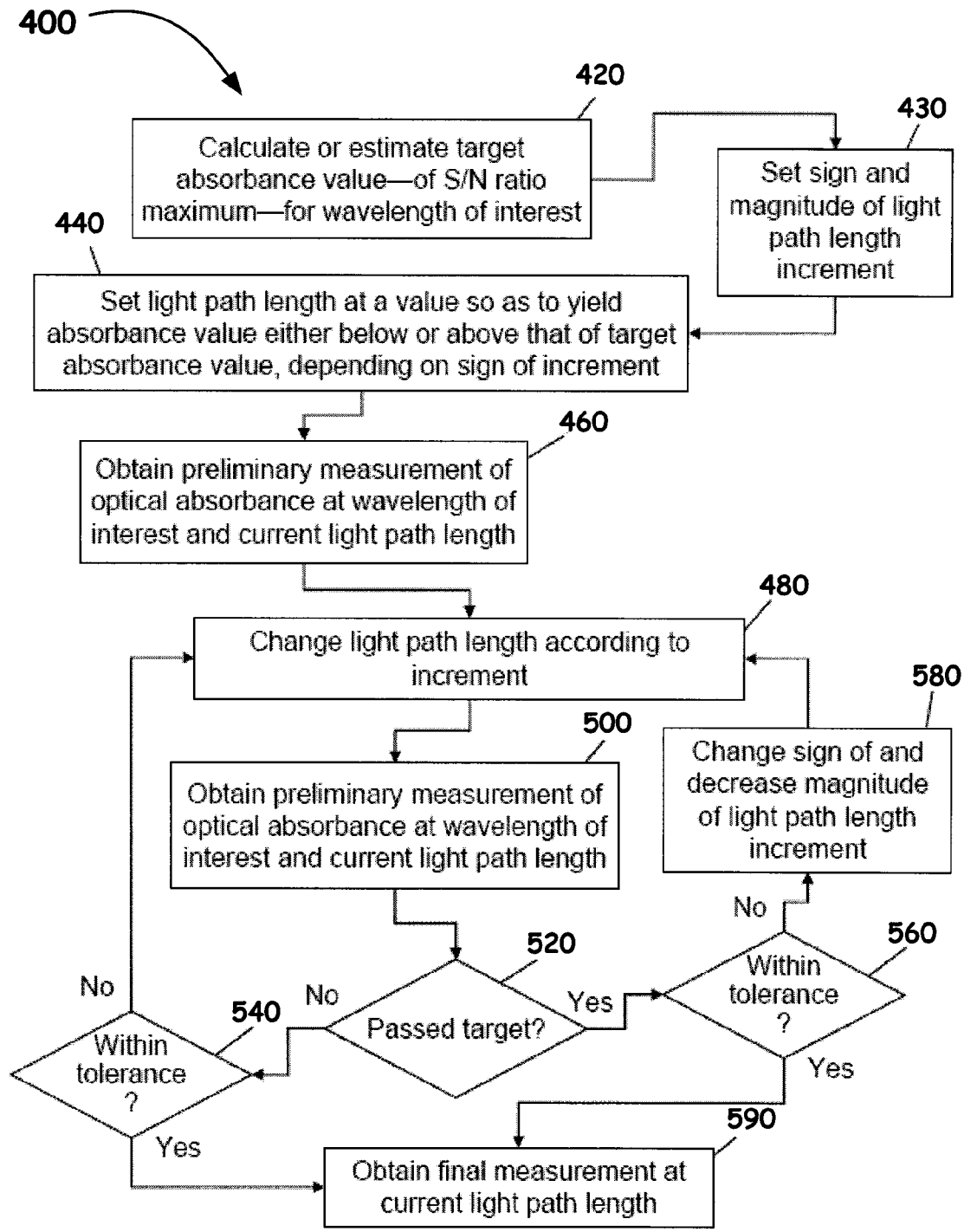
FIG. 12 is a flowchart of a second exemplary method in accordance with an embodiment of the invention.

Referring now to FIG. 12 step 420 of a method 400 of operation includes calculating or estimating a target absorbance value—that is, the absorbance value providing a maximum in S/N ratio for a wavelength of interest. Step 430 of the method 400 comprises setting the sign (corresponding to the direction of change) and magnitude of the light path length increment, ΔP, which will subsequently be used to scan through absorbance values. Note that the relative order of steps 420 and 430 can be reversed from that shown in FIG. 12. Step 440 includes setting the initial light path length, $P_0$, at a value so as to yield an expected absorbance value either below or above that of target absorbance value, depending on whether absorbance values are to be scanned from low-to-high or high-to-low, respectively. Step 460 includes obtaining a preliminary measurement of optical absorbance at the wavelength of interest and the current light path length. The subsequent step 480 includes changing the current light path length to a new value in accordance with the increment value set in step 430. In step 500, a preliminary measurement of optical absorbance at the wavelength of interest and the new current light path length is obtained.

In decision step 520, as shown in FIG. 12, a determination is made whether the measured absorbance that has been scanned passed the target absorbance calculated or estimated in step 420. Regardless of whether the target absorbance has been passed, the most recent change in light path length (step 480) may have caused the measured absorbance to be sufficiently close to the target absorbance—that is, within some tolerance of the target absorbance. Thus, if such is determined, in either decision step 540 or decision step 560, a final measurement is obtained, in the final step 590, at the current light path length. The final measurement is generally of higher quality or greater precision then any of the preliminary measurements, possibly by conducting the measurement for a longer period of time.

If the most recently measured absorbance in not within the tolerance of the target absorbance (step 540 or step 560), then the light path length should be changed and a new measurement obtained at the new light path length. If the absorbance has not been scanned past the target absorbance, then execution of the method passes directly from step 540 back to step 480. If the absorbance has been scanned past the target absorbance, then execution proceeds from step 560 to step 580, in which the sign (direction) of the light path length increment is changed so as to scan in a reverse sense. It may be desirable, in step 580, to also decrease the magnitude of the increment, so that the target absorbance is more precisely obtained. The loop defined by steps 480-580 may be repeated until the measured absorbance is within the tolerance of the target absorbance.

Figure 14:
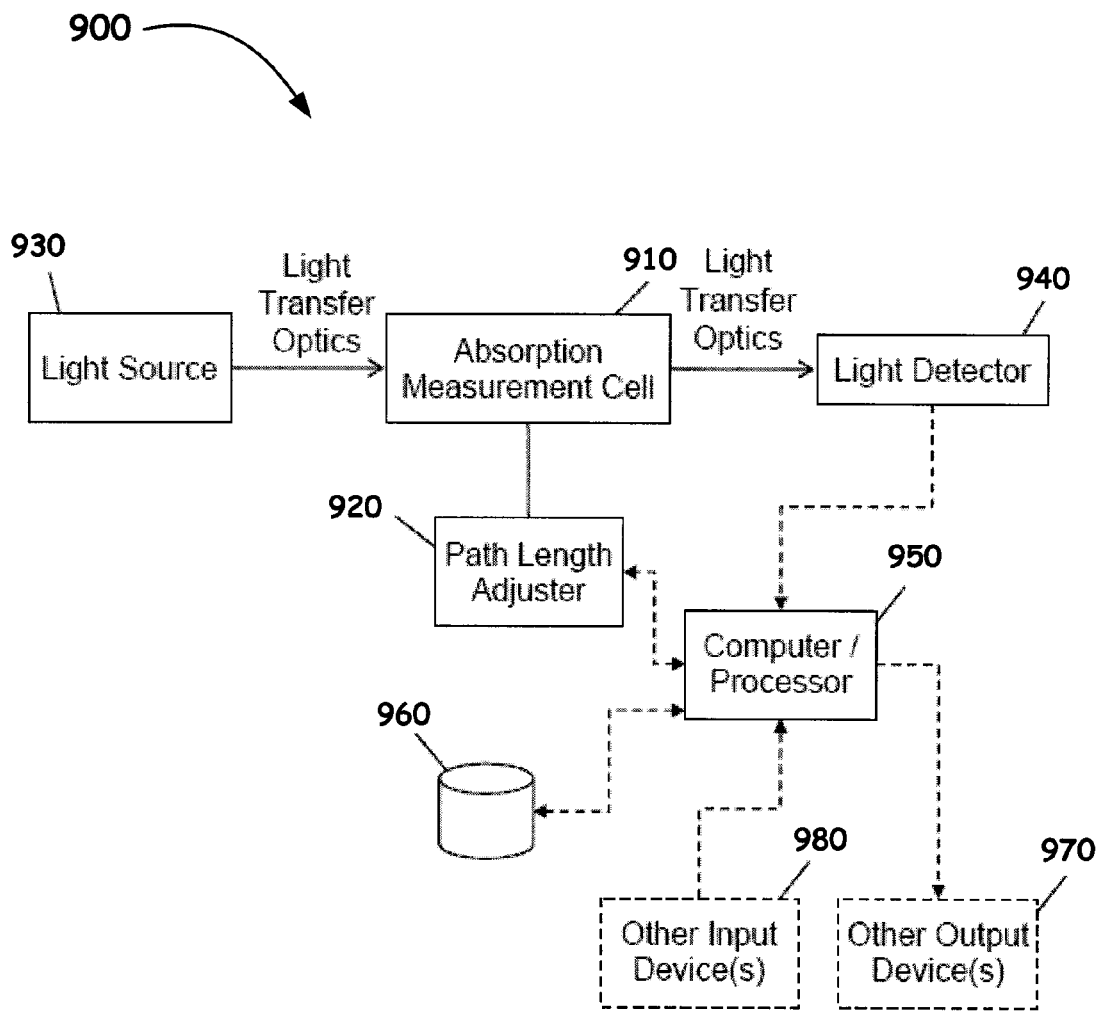
FIG. 14 is a schematic illustration of a system for automated optical absorbance measurements in accordance with an embodiment of the invention.

It is to be appreciated that the method of operation 400, or various selected steps thereof, can be carried out automatically by a system including a computer or other electronic processor and computer program instructions tangibly embodied on a computer readable medium, such as a disk drive, magnetic tape, optical disk drive, memory card, etc. One such system in accordance with an embodiment of the present invention is illustrated in FIG. 14. The system, generally designated by the reference numeral 900 includes an optical absorption measurement cell 910, a light path length adjuster 920 mechanically coupled to the optical absorption measurement cell, a light source 930 optically coupled to the optical absorption measurement cell and a light detector 940, also optically coupled to the optical absorption measurement cell. The system 900 further includes a computer or other electronic processor 950 electronically coupled to both the path length adjuster and to the light detector and a computer readable medium 960 electronically coupled to the computer or other electronic processor. The computer readable medium 960 may perform as both an input and an output device. Optionally, the computer/processor 950 may further be electronically coupled to one or more other output devices 970, such as display screens, printers, etc. and/or one or more other input devices 980, such as keyboards, internet connections, etc.

Dashed connecting lines in FIG. 14 represent connection pathways that carry electronic signals and the flow of electronic signal information. Arrows on the various connecting lines represent possible direction of flow of information or, alternatively, light propagation direction. The connecting lines between the light source and the absorption measurement cell and between the absorption measurement cell and the light detector implicitly include any necessary light transfer optics, such as optical fibers, lenses, prisms, mirrors, optical filters, etc.

Moreover, the absorption measurement cell 910 may be any of the absorption measurement cell apparatuses disclosed in the aforementioned U.S. Pat. Nos. 6,809,826 and 6,628, 382. Accordingly, the path length adjuster 920 can include any apparatus that is operable to mechanically vary the separation, P, between the anvils described in those patent documents (e.g., see FIG. 1 herein). The light source 930 may be any form of source of electromagnetic radiation, such as an incandescent lamp, an ionized gas lamp, a laser, a light emitting diode, etc. The light detector 940 may be any suitable light detector, such a photodiode, photodiode array, photomultiplier tube, charge-coupled device, etc.

In the system 900, the computer/processor 950 provides instructions to the path length adjuster 920 so as to command the path length adjuster to set the light path length within the absorption measurement cell 910 to a certain value. For example, the computer/processor may automatically send instructions to set or change light path length as in steps 440 and 480 of the method 400, as shown in FIG. 12. If the light path adjuster 920 also includes a position sensor, such position information may be returned to the computer processor 950 from the path length adjuster. The computer processor 950 also receives electronic signal information from the light detector 940 relating to the intensity (e.g., power) of light sensed by the light detector after transfer of such light from the absorption measurement cell. For instance, such signal reception may automatically occur during the measurement steps 460, 500, and 590 of the method 400. The computer/processor may also automatically perform the calculations and evaluate the decisions of steps 420, 520, 540, and 560 of method 400. It may also set the values of variables, such as in steps 430 and 560. The sequence of events performed by the computer/processor 950 may be controlled in accordance with program instructions stored on the computer readable medium 960 and transferred to the computer/processor therefrom. Results of the measurements—for instance, the results of the final measurement in step 590 of method 400—may also be transferred from the computer/processor 950 to the computer readable medium 960 for storage thereon. Output may also be provided to a user via output devices 970. The user may control program execution via input devices 980. For instance, the user can input parameters in steps 420 and 430 of method 400.

Experimental situations may occur in which a plurality of chemical compounds is present in a single sample. Some of these compounds may include analytes and others may comprise solvent components. For instance, in many situations, the sample may have only two chemical components in appreciable quantity—an analyte and a solvent, such as water. Suppose that there are (or may possibly be) n such chemical compounds in the sample, being referenced by the index i, where $1 \leq i \leq n$. Each such compound may be present at its own concentration, $c_i$, and each one of the analyte compounds may be associated with one or more wavelengths of interest at which absorbance measurements are to be obtained by, for instance, the apparatus 10 (FIGS. 1A-1B). Let the $j^{th}$ such wavelength of the $i^{th}$ compound (either analyte or solvent or other) be denoted by $\lambda_{i,j}$ and let the molar absorptivity of this compound at any wavelength $\lambda_k$ be denoted by $\epsilon_{i,k}$. Also, just for purposes of discussion, assume that there is a single target absorbance, $A_{target}$, which is independent of wavelength, $\lambda$. If there are a total of w wavelengths of interest, $\lambda_{i,j}$, then let these wavelengths be re-indexed in order of increasing wavelength as $\lambda_k$ where Then, from Eq. 3, there will be a plurality of target light path lengths, $P_k$, of the form:

$$P_k = \frac{A_{target}}{\sum_{i=1}^{n}(\varepsilon_{i,k}c_i)} \quad \text{Eq. 10}$$

$$(1 \leq k \leq w).$$

In the derivation of Eq. 10, absorbance of components is taken to be additive and the absorptivity of each compound, $\epsilon_i$, is assumed to be known, a priori, as a function of wavelength, from either prior measurements of known materials or from standard reference data such as spectra, tables, electronic databases, etc. The symbol $\epsilon_{i,k}$ is here defined by $\epsilon_{i,k} \equiv \epsilon_i(\lambda_k)$.

In situations such as described above with reference to Eq. 10, in which a plurality of chemical compounds is present in a single sample, measurements may be made simultaneously at several wavelengths, such as would be the case by dispersing light, after transmission through the sample, onto a multichannel detector such as a photodiode array or a charge-coupled-device (CCD) detector. In this fashion, the absorbance may be measured at each wavelength of interest, $\lambda_k$, at each path length of a sequence of stepped path lengths. From Eq. 3, the measured absorbance, $A_k$, at wavelength $\lambda_k$ and at each path length P, is $$A_k = P\sum_{i=1}^{n}\varepsilon_{i,k}c_i. \quad \text{Eq. 11}$$

Experimentally, the path length, P, may be stepped from low values to large values (or vice versa) and a preliminary set of values of $A_k$ (e.g., a preliminary absorbance spectrum) determined at each such step. The variation of each measured preliminary $A_k$ may then be determined versus path length, either by graphical plotting or by mathematical analysis. All such $A_k$ increases with P, and, in general, this increase is linear in P. However, because of the variations of the various $\epsilon_i$ with $\lambda$, these increases are not generally identical. Through interpolation, the target P value, $P_{target}(\lambda_k)$, at which each $A_k$ passes through $A_{target}$ (and at which the signal-to-noise characteristics are optimized for the measurement at $\lambda_k$) may be determined. The path length may subsequently set to be equal to each determined value of $P_{target}(\lambda_k)$, in turn, and a higher-quality measurement obtained in the vicinity of $\lambda_k$ with such setting. Since the $P_{target}$ values may not be identical for all $A_k$, this procedure may require several settings of the path length, P.

Figure 13:
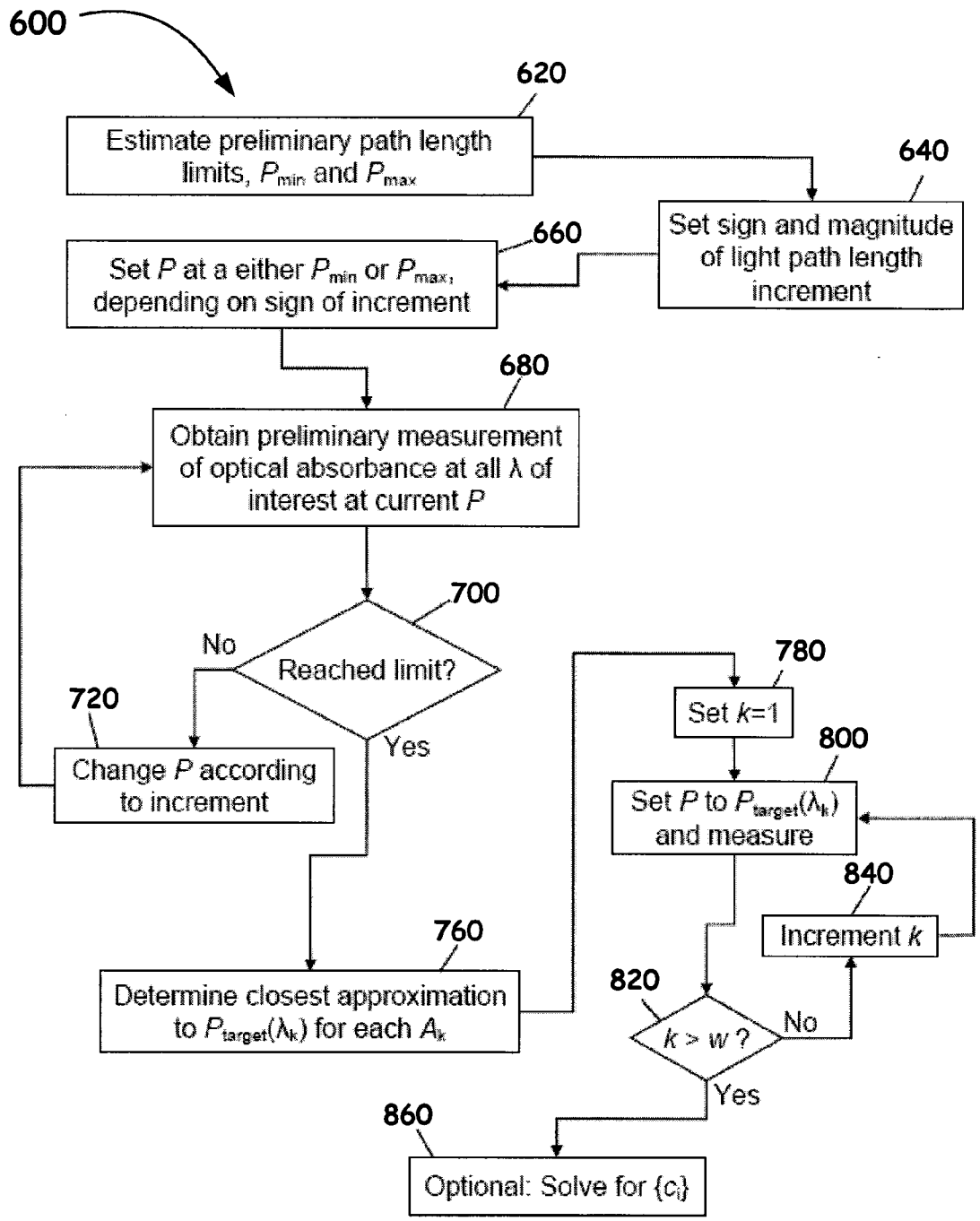
FIG. 13 is a flowchart of a third exemplary method in accordance with an embodiment of the invention.

The steps described above comprise a portion of an exemplary method in accordance with the present invention, method 600, which is illustrated in FIG. 13. In the first step, step 620 of the method 600, an estimation of the preliminary path length limits, $P_{min}$ and $P_{max}$ may be made. The parameters $P_{min}$ and $P_{max}$ are, respectively, the minimum and maximum light path lengths that will be required during the sequence of stepped path lengths. The parameter $P_{min}$ should be set small enough such that the expected sample absorbance is not greater than $A_{target}$ (within tolerance) for the wavelength of interest, $\lambda_k$, having the greatest value of the sum in the denominator of Eq. 10. Likewise, the parameter $P_{min}$ should be set large enough such that the expected sample absorbance is at least $A_{target}$ (within tolerance) for the wavelength of interest, $\lambda_k$, having the lowest value of the sum in the denominator of Eq. 10. In some cases, mechanical limits may prevent setting the path length to either $P_{min}$ or $P_{max}$ or both. In such cases, the relevant parameter(s) are set to the closest attainable value(s). Step 640 of method 600 includes setting the sign (corresponding to the direction of change) and magnitude of the light path length increment, $\Delta P$ that is to be subsequently used during the sequence of stepped path lengths. Note that the relative order of steps 620 and 640 can be reversed from that shown in FIG. 13.

Continuing with the discussion of method 600 in FIG. 13, the step 660 includes setting the light path length P at the starting value—either $P_{min}$ or $P_{max}$—depending on the sign of the light path length increment, $\alpha P$. The subsequent step 680 includes obtaining a preliminary measurement of optical absorbance at all $\lambda$ of interest (e.g., obtaining a preliminary absorbance spectrum) at the current P. In step 700, a determination is made as to whether the ending path length—either $P_{min}$ or $P_{max}$—has been reached. If not, then the path length P is changed according to the increment in step 720 and execution is returned to step 680. Once the ending path length has been reached in step 700, then, in step 760, the closest approximation to $P_{target}(\lambda_k)$ is determined for each $A_k$, possibly by interpolation, as previously described above. The result of this step is a set of w values of $P_{target}(\lambda_k)$, where $w \geq n$ and $1 \geq k \geq w$. In step 780, the index k is set to unity and the subsequent steps 800-840 include a loop in which P is set to each $P_{target}(\lambda_k)$, in turn, and a higher-quality absorbance measurement is obtained at each such setting. The final optional step, step 860 includes obtaining a solution (either an exact solution or a best fit solution) for the set $\{c_i\}$ of chemical compound concentrations using the absorbance measurements and the a priori known values of absorptivity. The concentrations of some components, such as solvents, may be simply assumed.

As before, the method of operation 600, or various selected steps thereof, can be carried out automatically by a system including a computer or other electronic processor and computer program instructions tangibly embodied on a computer readable medium. Such automatic steps could be carried out by the system 900 illustrated in FIG. 14, as previously discussed.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Such modifications and the like are considered simple modifications that are well within the ability of one of ordinary skill in the art and within the scope and spirit of the invention. Accordingly, many such modifications may be made by one of ordinary skill in the art without departing from the spirit, scope and essence of the invention. Neither the description, drawings nor the terminology is intended to limit the scope of the invention—the invention is defined by the claims.

What is claimed is:

1. An apparatus for measuring an optical property of a sample constrained by surface tension, comprising:
    a first pedestal surface coupled to a first optical conduit having a transmitting end;
    a base plate;
    a second pedestal surface mechanically coupled to said base plate and configured to receive a first liquid sample, said second pedestal surface being coupled to a second optical conduit having a receiving end, wherein said second pedestal further is operable so as to adjust a separation between said first and said second pedestal at a variable distance (P) to pull said first liquid sample into a column so as to be contained by surface tension, thereby providing an optical path with said transmitting end of said first optical conduit and said receiving end of said second optical conduit for photometric or spectrometric measurement; and
    a board configured with a sensor to provide feedback so as to enable precision displacement between said first and said second pedestal surfaces so as to enable said variable distance (P), said board further configured to enable holding a linear actuator motor body to said apparatus and thus:
    c) permit translational movement of said board together with said second optical conduit parallel to the axis of second optical conduit, and
    d) prevent rotation of said board and said second optical conduit with respect to said apparatus as a whole; thereby resulting in linear travel with minimal rotational effects and minimal change in optical alignment of second optical conduit with respect to said first optical conduit.

2. The apparatus of claim 1, wherein said board comprises a printed circuit board and said sensor configured on said printed circuit board comprises an eddy current sensor which is adapted to use a back plate of said linear actuator motor body as the object in which the Eddy currents are generated.

3. The apparatus of claim 2, wherein a changing circuit impedance resulting from the spacing of an inductor on said printed circuit board relative to said back plate of said linear actuator motor body changes the resonant frequency of the circuit on said printed circuit board, wherein a coupled digital circuit counts resultant pulses in a time interval to determine said circuit board to said coupled actuator motor back plate spacing so as to provide for a desired said optical path length.

4. The apparatus of claim 3, wherein said changing circuit impedance is monitored so as to resolve micron-size displacements that enables path length measurements from about 1 mm down to about 50 microns accuracy.

5. The apparatus of claim 1, wherein said board is configured with one or more slots that ride on one or more fasteners to enable holding said linear actuator motor body to said apparatus.

6. The apparatus of claim 1, wherein said apparatus measures absorbances from about 0.005 up to about 2.0 Absorbance Units for any given path length.

7. The apparatus of claim 1, wherein said board comprises a position sensor that establishes a reference position when a translation control system initializes upon startup or upon being interrupted by an opto-interrupter device.

8. The apparatus of claim 1, wherein said second optical conduit comprises an optical fiber, said optical fiber being disposed within an externally threaded holder, wherein a nut having an internally threaded portion is mechanically engaged with said externally threaded portion of said holder; wherein said linear actuator motor is mechanically coupled to said nut and operable so as to rotate said nut and induce said holder to move so as to adjust said distance, P.

9. The apparatus of claim 1, wherein said first and said second optical conduits comprise at least one optical fiber selected from: a single-mode fiber, a polarization maintaining fiber, and a multi-mode fiber.

10. The apparatus of claim 1, wherein said apparatus comprises an illumination source configured to provide wavelengths from about 190 nm up to about 840 nm.

11. A method of measuring a chemical concentration of a material constrained by surface tension, comprising:

- determining a target optical absorbance value so as to provide an optimal signal-to-noise ratio for a measurement of optical absorption;
- experimentally determining an optimal light path length through the material corresponding to said target optical absorbance value, said step of experimentally determining an optimal light path length to further include: providing a coupled printed circuit board configured with a sensor to provide feedback so as to enable precision displacements of a second pedestal surface with respect to a first pedestal surface so as to provide a variable distance (P) wherein said variable distance is adjusted to pull said material into a column so as to be contained by surface tension, said board being further configured to enable linear travel of said second pedestal with minimal rotational effects and minimal change in alignment with respect to said first pedestal surface;
- setting a light path length through said material substantially equal to said experimentally determined optimal light path length,
- measuring optical absorption through said set light path length of said material; and
- calculating the chemical concentration of said material from a known absorptivity of the material, the set light path length, and the measured optical absorption through said set light path length of said material.

12. The method of claim 11, wherein said step of determining a target optical absorbance value so as to provide an optimal signal-to-noise ratio further comprises: assuming a fixed noise component with respect to units of signal.

13. The method of claim 11, wherein said step of experimentally determining an optimal light path length further comprises:

a) setting a light path length at an absorbance value below or above that of said target absorbance value;
b) obtaining a measurement of the optical absorbance of said material;
c) incrementing via a known sign and magnitude said light path length;
d) obtaining a measurement of the optical absorbance of said material; and
e) repeating step c-d above until said target optical absorbance value is found.

14. The method of claim 11, wherein said precision displacements comprises path length measurements from about 1 mm down to about 50 microns accuracy.

15. The method of claim 11, wherein said measuring optical absorption step comprises: measuring absorbances from about 0.005 up to about 2.0 Absorbance Units for any given path length.

16. The method of claim 11, wherein said step of measuring optical absorption through said set light path length of said material comprises illuminating said sample with wavelengths from about 190 nm up to about 840 nm.

* * * * *